(12) United States Patent
Von Itter et al.

(10) Patent No.: US 12,715,141 B2
(45) Date of Patent: Aug. 25, 2026

(54) SETTING AND USING SOFTWARE REMOTE CENTERS OF MOTION FOR COMPUTER-ASSISTED SYSTEMS

(71) Applicant: INTUITIVE SURGICAL OPERATIONS, INC., Sunnyvale, CA (US)

(72) Inventors: Janice M. Von Itter, Oakland, CA (US); Nandini Devi Gurunathan, Cupertino, CA (US); Nathan C. Ho, Fremont, CA (US); Robert D. Kahn, Gilroy, CA (US); Goran A. Lynch, Oakland, CA (US); Lucas A Reilly, Campbell, CA (US); Amin Zeiaee, Los Gatos, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 26 days.

(21) Appl. No.: 18/851,351

(22) PCT Filed: Mar. 27, 2023

(86) PCT No.: PCT/US2023/016458
§ 371 (c)(1),
(2) Date: Sep. 26, 2024

(87) PCT Pub. No.: WO2023/192204
PCT Pub. Date: Oct. 5, 2023

(65) Prior Publication Data

US 2025/0205900 A1 Jun. 26, 2025

Related U.S. Application Data

(60) Provisional application No. 63/324,587, filed on Mar. 28, 2022.

(51) Int. Cl.
*B25J 9/16* (2006.01)
*A61B 34/35* (2016.01)
*B25J 15/00* (2006.01)

(52) U.S. Cl.
CPC ............. *B25J 9/1697* (2013.01); *A61B 34/35* (2016.02); *B25J 15/0019* (2013.01)

(58) Field of Classification Search
CPC ................... G06T 7/74; G06T 2200/04; G06T 2207/10028; G06T 2207/30201;
(Continued)

(56) References Cited

U.S. PATENT DOCUMENTS 6,671,391 B1 * 12/2003 Zhang .................. G06V 40/161 382/118
6,804,391 B1 * 10/2004 Blake .................. G06V 10/764 706/45
(Continued)

FOREIGN PATENT DOCUMENTS

CN 113180828 A 7/2021
JP 2021035507 A 3/2021
(Continued)

OTHER PUBLICATIONS

International Preliminary Report on Patentability for Application No. PCT/US2023/016458, mailed Oct. 10, 2024, 11 pages.
(Continued)

*Primary Examiner* — Bhavesh V Amin
(74) *Attorney, Agent, or Firm* — Artegis Law Group, LLP

(57) ABSTRACT

Setting and using a software remote center of motion (RCM) for a computer-assisted system including an input control, a repositionable structure comprising a plurality of joints, and a processing system. The processing system is configured to: receive a proposed position for a software RCM of the repositionable structure; determine whether to accept the
(Continued)

proposed position based on a geometric relationship between a position of a hardware RCM and the proposed position; in response to determining to accept the proposed position, set a current position of the software RCM based on the proposed position; after setting the current position and in response to an indication to move the repositionable structure with a desired motion, determine a commanded motion of the joints to move the repositionable structure in accordance with the desired motion while maintaining the current position of the software RCM; and drive the joints in accordance with the commanded motion.

29 Claims, 7 Drawing Sheets

(58) Field of Classification Search
CPC ......... G06T 7/50; G06T 7/73; G06T 2200/24; G06T 2207/10032; G06T 2207/20084; G06T 2207/20104; G06T 2207/30244; G06T 7/579; G06V 10/24; G06V 10/7515; G06V 10/76; G06V 20/597; G06V 20/64; G06V 40/161; G06V 40/164; G05D 1/0808; G05D 1/0038; G01P 15/00; B25J 9/1697; B25J 15/0019; A61B 34/35; A61B 34/37; A61B 34/30
See application file for complete search history.

(56) References Cited

U.S. PATENT DOCUMENTS 6,804,416 B1 * 10/2004 Bachelder ............... G06F 18/40 345/651
6,959,109 B2 * 10/2005 Moustafa ............. G06V 10/242 382/117
7,313,266 B2 * 12/2007 Ishiyama ............. G06V 40/162 345/582
7,620,202 B2 * 11/2009 Fujimura ........... G06V 10/7515 348/169
8,004,229 B2 8/2011 Nowlin et al.
8,031,906 B2 * 10/2011 Fujimura ............. G06V 20/597 348/169
8,253,746 B2 * 8/2012 Geisner ................... G06F 3/017 345/474
8,264,536 B2 * 9/2012 McEldowney ...... G06V 10/145 348/135
8,267,781 B2 * 9/2012 Geiss .................... A63F 13/428 463/31
8,290,249 B2 * 10/2012 Mathe .................... G06V 10/40 382/154
8,369,574 B2 * 2/2013 Hu ..................... G06V 30/2504 382/103
8,374,423 B2 * 2/2013 Lee ......................... G06T 7/254 382/103
8,541,970 B2 9/2013 Nowlin et al.
8,620,473 B2 12/2013 Diolaiti et al.
8,624,537 B2 1/2014 Nowlin et al.
8,682,087 B2 * 3/2014 Tian ....................... H04N 19/82 382/233
8,749,189 B2 6/2014 Nowlin et al.
8,749,190 B2 6/2014 Nowlin et al.
8,786,241 B2 7/2014 Nowlin et al.
8,816,628 B2 8/2014 Nowlin et al.
8,823,308 B2 9/2014 Nowlin et al.
8,861,893 B2 * 10/2014 Chen ..................... G06T 3/4053 348/14.02
8,903,546 B2 12/2014 Diolaiti et al.
9,084,623 B2 7/2015 Gomez et al.
9,107,683 B2 8/2015 Houtash et al.
9,138,129 B2 9/2015 Diolaiti
9,345,544 B2 5/2016 Hourtash et al.
9,468,501 B2 10/2016 Hourtash et al.
9,492,235 B2 11/2016 Hourtash et al.
9,492,927 B2 11/2016 Diolaiti et al.
9,517,106 B2 12/2016 Hourtash et al.
9,586,323 B2 3/2017 Diolaiti et al.
9,675,421 B2 6/2017 Hourtash et al.
9,844,415 B2 12/2017 Hourtash
9,907,619 B2 3/2018 Hourtash et al.
10,299,883 B2 5/2019 Kilroy et al.
10,327,855 B2 6/2019 Hourtash et al.
10,376,337 B2 8/2019 Kilroy et al.
10,383,699 B2 8/2019 Kilroy et al.
10,513,031 B2 12/2019 Hourtash
10,828,115 B2 11/2020 Koenig et al.
10,987,192 B2 4/2021 Garcia et al.
11,220,009 B2 * 1/2022 Sasagawa ............ G06V 40/172
11,511,890 B2 * 11/2022 Murakami ............. G01D 21/02
2004/0189720 A1 * 9/2004 Wilson .................... G06F 3/017 715/863
2004/0193413 A1 * 9/2004 Wilson ................. H04N 13/239 382/209
2005/0058337 A1 * 3/2005 Fujimura ............... G06V 10/76 382/159
2005/0265583 A1 * 12/2005 Covell .................... G06T 7/251 382/106
2006/0033713 A1 * 2/2006 Pryor ..................... G06V 40/20 345/158
2010/0034427 A1 * 2/2010 Fujimura ............... G06V 10/76 382/106
2014/0344718 A1 * 11/2014 Rapaport .............. H04L 67/306 715/753
2015/0025549 A1 1/2015 Kilroy et al.
2015/0032126 A1 1/2015 Nowlin et al.
2015/0051733 A1 2/2015 Nowlin et al.
2019/0343594 A1 11/2019 Garcia Kilroy et al.
2020/0022775 A1 1/2020 Garcia Kilroy et al.
2021/0012520 A1 * 1/2021 Zhou .................... G05D 1/0038
2021/0045817 A1 2/2021 Koenig et al.
2021/0114750 A1 * 4/2021 Murakami ................ B64F 5/60
2021/0330405 A1 10/2021 Gonenc et al.
2021/0401515 A1 12/2021 Rockrohr et al.

FOREIGN PATENT DOCUMENTS

WO WO-2006124390 A2 11/2006
WO WO-2013071057 A1 5/2013
WO WO-2013071071 A1 5/2013
WO WO-2013181503 A1 12/2013
WO WO-2013181507 A1 12/2013
WO WO-2013181516 A1 12/2013
WO WO-2014028703 A1 2/2014
WO WO-2014146095 A1 9/2014
WO WO-2014146107 A1 9/2014
WO WO-2014146119 A1 9/2014
WO WO-2014146120 A1 9/2014
WO WO-2016044574 A1 3/2016
WO WO-2021061105 A1 4/2021
WO WO-2021067461 A1 4/2021
WO WO-2022046787 A1 3/2022

OTHER PUBLICATIONS

International Search Report and Written Opinion for Application No. PCT/US2023/016458, mailed Jun. 7, 2023, 17 pages.
Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

SETTING AND USING SOFTWARE REMOTE CENTERS OF MOTION FOR COMPUTER-ASSISTED SYSTEMS

RELATED APPLICATIONS

This application is a U.S. National Stage patent application of International Patent Application No. PCT/US2023/016458, filed Mar. 27, 2023, and claims the benefit to U.S. Provisional Application No. 63/324,587, filed Mar. 28, 2022, and entitled "Setting and Using Software Remote Centers of Motion for Computer-Assisted Systems," each of these related applications are incorporated by reference herein.

TECHNICAL FIELD

The present disclosure relates generally to computer-assisted systems and more particularly to setting and using software remote centers of motion for computer-assisted systems.

BACKGROUND

Computer-assisted systems are often used to perform or assist procedures in a workspace. In an example computer-assisted system with teleoperation, an operator at a user input system manipulates a leader device (e.g., an input device configured to accept commands for a follower device) to cause motions of a follower device (e.g., a manipulating assembly that can be teleoperated, and comprising a repositionable structure with or without a supported instrument). In an example, motions of the leader device relative to an operator frame of reference are used to determine corresponding motion commands for the follower device relative to a field of view of an imaging device.

In some examples, a computer-assisted system comprises a repositionable structure with a remote center of motion (RCM) enforced by the hardware design of the repositionable structure. That is, this "hardware" RCM experiences little to no motion during a task performed by the repositionable structure because the joints that are driven to enable the repositionable structure to perform the task are physically designed not to disturb this hardware RCM.

In some instances, it may be desirable to drive a repositionable structure with a hardware RCM to move about an RCM not collocated with the hardware RCM. For example, the ability to drive the repositionable structure to move about RCMs other than a fixed hardware RCM can help increase range of movement, increase the flexibility and dexterity of the repositionable structure, save time, reduce power or energy required to move the repositionable structure, and/or the like.

Accordingly, techniques for setting and using a software remote center of motion of a computer-assisted system are desirable.

SUMMARY

Consistent with some embodiments, a computer-assisted system includes an input control; a repositionable structure comprising a plurality of joints, wherein each joint of a first joint set of the plurality of joints is physically restricted to joint motions that maintain a position of a hardware remote center of motion (RCM) of the repositionable structure, and wherein each joint of a second joint set of the plurality of joints is physically configured to perform joint motions capable of translating the position of the hardware RCM; and a processing system communicatively coupled to the input control and the repositionable structure. The processing system is configured to: receive an indication of a proposed position for a software RCM of the repositionable structure, determine whether to accept the proposed position based on a geometric relationship between the position of the hardware RCM and the proposed position, in response to a determination to accept the proposed position, set a current position of the software RCM based on the proposed position, after setting the current position of the software RCM based on the proposed position and in response to an indication to move the repositionable structure with a desired motion, determine a commanded motion of the plurality of joints to move the repositionable structure in accordance with the desired motion while maintaining the current position of the software RCM, and drive the plurality of joints in accordance with the commanded motion.

Consistent with some embodiments, a method performed by a processing system includes receiving, by the processing system, an indication of a proposed position for a software remote center of motion (RCM) for a repositionable structure; determining, by the processing system, whether to accept the proposed position based on a geometric relationship between a position of a hardware RCM of the repositionable structure and the proposed position; in response to a determination to accept the proposed position, setting, by the processing system, a current position of the software RCM based on the proposed position; after setting the current position of the software RCM based on the proposed position and in response to an indication to move the repositionable structure with a desired motion, determining, by the processing system, a commanded motion of a plurality of joints to move the repositionable structure in accordance with the desired motion while maintaining the current position of the software RCM; and driving, by the processing system, the plurality of joints in accordance with the commanded motion, wherein each joint of a first joint set of the plurality of joints is physically restricted to joint motions that maintain a position of a hardware RCM of the repositionable structure, and wherein each joint of a second joint set of the plurality of joints is physically configured to perform joint motions capable of translating the position of the hardware RCM.

Consistent with some embodiments, one or more non-transitory machine-readable media include a plurality of machine-readable instructions which when executed by one or more processors are adapted to cause the one or more processors to perform any of the methods described herein.

Figure 1:
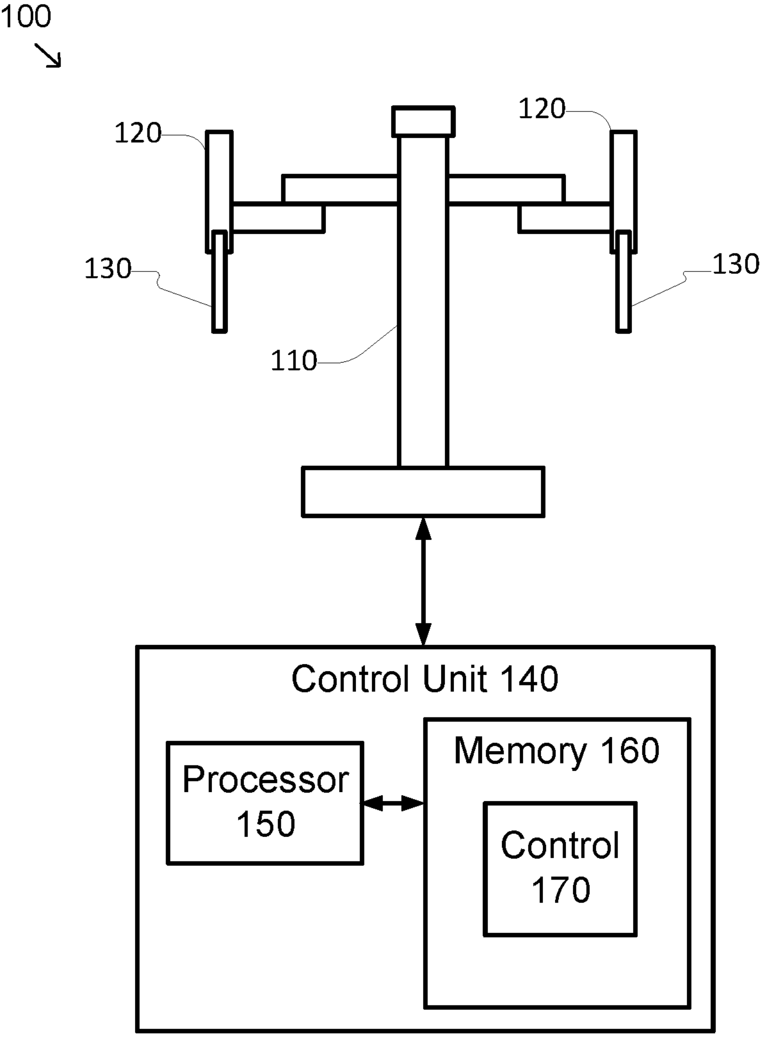
FIG. 1 is a diagram of a computer-assisted system in accordance with one or more embodiments.

In the figures, elements having the same designations have the same or similar functions.

DETAILED DESCRIPTION

In this description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

Further, the terminology in this description is not intended to limit the invention. For example, spatially relative terms—such as "beneath", "below", "lower", "above", "upper", "proximal", "distal", and the like—may be used to describe the relation of one element or feature to another element or feature as illustrated in the figures. These spatially relative terms are intended to encompass different positions (i.e., locations) and orientations (i.e., rotational placements) of the elements or their operation in addition to the position and orientation shown in the figures. For example, if the content of one of the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly. Likewise, descriptions of movement along and around various axes include various special element positions and orientations. In addition, the singular forms "a", "an", and "the" are intended to include the plural forms as well, unless the context indicates otherwise. And, the terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

Elements described in detail with reference to one embodiment, implementation, or module may, whenever practical, be included in other embodiments, implementations, or modules in which they are not specifically shown or described. For example, if an element is described in detail with reference to one embodiment and is not described with reference to a second embodiment, the element may nevertheless be claimed as included in the second embodiment. Thus, to avoid unnecessary repetition in the following description, one or more elements shown and described in association with one embodiment, implementation, or application may be incorporated into other embodiments, implementations, or aspects unless specifically described otherwise, unless the one or more elements would make an embodiment or implementation non-functional, or unless two or more of the elements provide conflicting functions.

In some instances, well known methods, procedures, components, and circuits have not been described in detail so as not to unnecessarily obscure aspects of the embodiments.

This disclosure describes various devices, elements, and portions of computer-assisted systems and elements in terms of their state in three-dimensional space. As used herein, the term "position" refers to the location of an element or a portion of an element in a three-dimensional space (e.g., three degrees of translational freedom along Cartesian x-, y-, and z-coordinates). As used herein, the term "orientation" refers to the rotational placement of an element or a portion of an element (three degrees of rotational freedom—e.g., roll, pitch, and yaw, angle-axis, rotation matrix, quaternion representation, and/or the like). As used herein, the term "shape" refers to a set positions or orientations measured along an element. As used herein, and for a device with a kinematic chain, such as a with repositionable structure with a plurality of links coupled by one or more joints, the term "proximal" refers to a direction toward a base of the kinematic chain, and "distal" refers to a direction away from the base along the kinematic chain.

As used herein, the term "pose" refers to the multi-degree of freedom (DOF) spatial position and orientation of a coordinate system of interest attached to a rigid body. In general, a pose includes a pose variable for each of the DOFs in the pose. For example, a full 6-DOF pose would include 6 pose variables corresponding to the 3 positional DOFs (e.g., x, y, and z) and the 3 orientational DOFs (e.g., roll, pitch, and yaw). A 3-DOF position only pose would include only pose variables for the 3 positional DOFs. Similarly, a 3-DOF orientation only pose would include only pose variables for the 3 rotational DOFs. Further, a velocity of the pose captures the change in pose over time (e.g., a first derivative of the pose). For a full 6-DOF pose, the velocity would include 3 translational velocities and 3 rotational velocities. Poses with other numbers of DOFs would have a corresponding number of velocities translational and/or rotational velocities.

Aspects of this disclosure are described in reference to computer-assisted systems, which may include devices that are teleoperated, externally manipulated, autonomous, semiautonomous, and/or the like. Further, aspects of this disclosure are described in terms of an implementation using a teleoperated surgical system, such as the da Vinci® Surgical System commercialized by Intuitive Surgical, Inc. of Sunnyvale, California. Knowledgeable persons will understand, however, that inventive aspects disclosed herein may be embodied and implemented in various ways, including teleoperated and non-teleoperated, and medical and non-medical embodiments and implementations (e.g., medical and non-medical instruments, devices, or systems). Implementations on da Vinci® Surgical Systems are merely exemplary and are not to be considered as limiting the scope of the inventive aspects disclosed herein. For example, techniques described with reference to surgical instruments and surgical methods may be used in other contexts. Thus, the instruments, systems, and methods described herein may be used for humans, animals, portions of human or animal anatomy, industrial systems, general robotic, or teleoperated systems. As further examples, the instruments, systems, and methods described herein may be used for non-medical purposes including industrial uses, general robotic uses, sensing or manipulating non-tissue work pieces, cosmetic improvements, imaging of human or animal anatomy, gathering data from human or animal anatomy, setting up or taking down systems, training medical or non-medical personnel, and/or the like. Additional example applications include use for procedures on tissue removed from human or animal anatomies (with or without return to a human or animal anatomy) and for procedures on human or animal cadavers. Further, these techniques can also be used for medical treatment or diagnosis procedures that include, or do not include, surgical aspects.

FIG. 1 is a diagram of a computer-assisted system 100 in accordance with one or more embodiments. As shown in the example of FIG. 1, the computer-assisted system 100 includes a manipulating assembly 110 with one or more repositionable structures 120. In the example of FIG. 1, the repositionable structure(s) are shown as manipulator arms comprising a plurality of links coupled by one or more joints. Each of the one or more repositionable structures 120 can support one or more instruments 130. In some examples, the manipulating assembly 110 can comprise a computer-assisted surgical assembly. Examples of medical instruments include surgical instruments for interacting with tissue, imaging, sensing devices, and/or the like. In some examples, the instruments 130 can include end effectors that are capable of, but are not limited to, performing, gripping, retracting, cauterizing, ablating, suturing, cutting, stapling, fusing, sealing, etc., and/or combinations thereof.

In a teleoperation example, the manipulating assembly 110 can further be communicatively coupled by wired or wireless connection to a user input system (not shown). The user input system can include one or more input controls, also referred to herein as input devices, for operating the manipulating assembly 110, the one or more repositionable structures 120, and/or the instruments 130. In some examples, the one or more input controls can include kinematic chains of links and one or more joint(s), one or more actuators for driving portions of the input control(s), robotic manipulators, levers, pedals, switches, keys, knobs, triggers, and/or the like.

In examples supporting external manipulation, the input controls may be located at the repositionable structure. As a specific example, the input controls may comprise joint sensors that detect joint deflection, and the computer-assisted system is configured to process certain joint deflections to be commands to move the joint.

The manipulating assembly 110 of FIG. 1 is coupled to a control unit 140 via an interface. The interface can be wired and/or wireless, and can include one or more cables, fibers, connectors, and/or buses and can further include one or more networks with one or more network switching and/or routing devices. Operation of the control unit 140 is controlled by a processor 150. And although the control unit 140 is shown with only one processor 150, it is understood that the processor 150 is representative of one or more central processing units, multi-core processors, microprocessors, microcontrollers, digital signal processors, field programmable gate arrays (FPGAs), application specific integrated circuits (ASICs), graphics processing units (GPUs), tensor processing units (TPUs), and/or the like in the control unit 140. The control unit 140 can be implemented as a stand-alone subsystem and/or board added to a computing device or as a virtual machine. In some embodiments, the control unit 140 can be included as part of the user input system and/or the manipulating assembly 110, and/or be operated separately from, and in coordination with, the user input system and/or the manipulating assembly 110.

As one example, the manipulating assembly 110, the user input system, and/or the control unit 140 may correspond to the patient side cart, the surgeon console, and the processing units and associated software of da Vinci® Surgical System commercialized by Intuitive Surgical, Inc. of Sunnyvale, California. In some embodiments, manipulating assemblies with other configurations, such as fewer or more repositionable structures, different user input systems or input controls, different repositionable structure hardware, and/or the like, can comprise the computer-assisted system 100.

The memory 160 can be used to store software executed by the control unit 140 and/or one or more data structures used during operation of the control unit 140. The memory 160 can include one or more types of machine-readable media. Some common forms of machine-readable media can include floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip, or cartridge, and/or any other medium from which a processor or computer is adapted to read.

As shown in the example of FIG. 1, the memory 160 includes a control module 170 that can be used to support autonomous, semiautonomous, and/or teleoperated control of the manipulating assembly 110. The control module 170 can include one or more application programming interfaces (APIs) for receiving position, motion, force, torque, and/or other sensor information from the manipulating assembly 110, the repositionable structures 120, and/or the instruments 130, for sharing position, motion, force, torque, and/or collision avoidance information with other control units regarding other devices, and/or planning and/or assisting in the planning of motion for the manipulating assembly 110 (such as motion of the repositionable structures 120), and/or the instruments 130. In some examples, the control module 170 further supports autonomous, semiautonomous, and/or teleoperated control of the manipulating assembly 110 and/or the instruments 130 during the performance of various tasks. And although the control module 170 is depicted as a software application, the control module 170 can optionally be implemented using hardware, software, and/or a combination of hardware and software.

In a teleoperation example for computer-assisted system 100, an input control comprises a leader device (also called a "master" device in industry), and the manipulating assembly 110 or a repositionable structure 120 (either supporting or not supporting an instrument 130) comprises a follower device (also called a "slave" device in industry). An operator can use the one or more input controls to command motion of the manipulating assembly 110, such as by commanding motion of one or more repositionable structures 120 and/or instruments 130, in a leader-follower configuration. The leader-follower configuration is a type of teleoperation configuration, and is sometimes called a master-slave configuration in industry.

In some medical embodiments, the computer-assisted system 100 can be found in a clinic, diagnostic facility, an operating room, an interventional suite, or other medical environment. Although the computer-assisted system 100 is shown comprising one manipulating assembly 110 with two repositionable structures 120, each supporting a corresponding instrument 130, one of ordinary skill would understand that the computer-assisted system 100 can include any number of manipulating assemblies, each manipulating assembly may comprise one or more repositionable structures, and each repositionable structure may support one or more instruments, and that all of these elements may be similar or different in design from that specifically depicted in these figures. For example, in some examples, each of the manipulating assemblies can include fewer or more repositionable structures, and/or support fewer or more instruments, than specifically depicted in these figures.

In some implementations, each of the one or more repositionable structures 120 comprise a plurality of joints, where the plurality of joints includes multiple joint sets of drivable joints. Drivable joints can be driven by actuators to move the joint, and thus move components physically coupled to the joint. A joint set includes one or more joints of the plurality of joints. The joint(s) of a first joint set of drivable joints are, by mechanical configuration, constrained to produce motion that pivot an RCM-constrained link (e.g., a distal link) of the plurality of links of the repositionable assembly about a hardware RCM, or that translate the RCM-constrained link along a linear axis intersecting the hardware RCM. Thus, the joint(s) of the first joint set, when driven to move the repositionable structure, do not translate this hardware RCM, such that the first joint set of drivable joints are physically designed not to move the hardware RCM.

The joint(s) of a second joint set of drivable joints of the repositionable structure, are by mechanical configuration capable of translating the hardware RCM. During some instances of operation, the first and second joint sets of drivable joints are driven at different times, such that the second joint set of drivable joints is not driven when the first joint set of drivable joints is driven. For example, in an example where the second joint set is used for setup and the first joint set is used for performing a task, the system can drive the second joint set before the task is performed, to move and then locate the hardware RCM in space. In this example, the second joint set is then not driven to move the hardware RCM during the procedure, and the first joint set is driven to enable the repositionable structure to perform the procedure. In this example, the computer-assisted system uses a hardware RCM, and the position of the hardware RCM is held static during the procedure.

In some use cases, the hardware RCM can be placed at an entry into a workspace, such as an opening into a chamber or device, a surgical incision, a natural orifice such as a mouth or throat, and/or the like. End effectors of instrument(s) or repositionable structure(s) located distally from the hardware RCM are translated and rotated by driving the first joint set to produce pivoting motions about the hardware RCM.

In some instances, it is desirable to move the end effectors of instrument(s) or repositionable structure(s) in motions other than easily achievable with a static RCM. For example, some repositionable structure and/or instrument design may limit the ability of the end effectors to reach and interact with particular regions, such as regions that are too close to, or too far from, the hardware RCM. This limitation can be overcome in such implementations by re-locating the hardware RCM, such as by moving the hardware RCM to be further retracted from the entry (perhaps to reach regions closer to the entry) or to be further inserted into the entry or workspace (perhaps to reach regions further from the entry).

However, in some examples, locating the hardware RCM away from the entry into the workspace can cause undesirable motion of the repositionable structure (or an instrument supported by the repositionable structure) relative to the entry. For example, in some instances, lateral motion of the repositionable structure (or instrument) relative to the entry can cause undesirable collisions or applied forces with material near the entry. In a medical example, lateral motion of an instrument in a surgical incision can cause further tissue trauma. Further, in some examples, the ability to relocate the RCM dynamically can provide advantages such as greater end effector reach, greater overall range of motion, decreased motion relative to a position other than at the position of the hardware RCM, (such as for collision avoidance), and the like.

Figure 2:
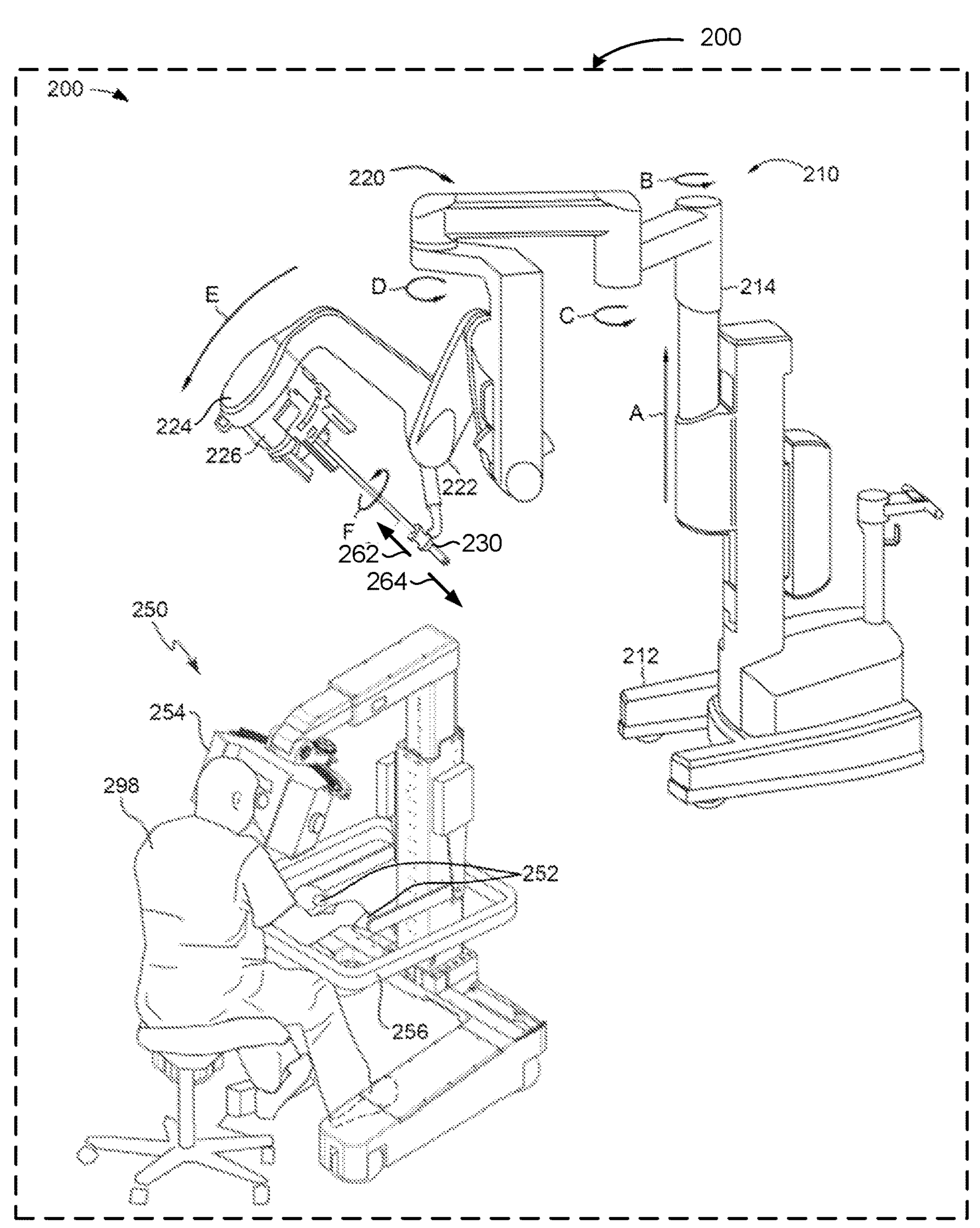
FIG. 2 is a diagram of a computer-assisted system in accordance with one or more embodiments.

FIG. 2 is a diagram of a computer-assisted system 200 in accordance with one or more embodiments. The computer-assisted system 200, in the example of FIG. 2, includes a repositionable structure shown as a manipulating assembly 210 and a user input system 250. In a teleoperation scenario, an operator 298 can use the user input system 250 to operate the manipulating assembly 210, such as in a leader-follower configuration. In the leader-follower configuration for the example of FIG. 1, a component of the user input system 250 (e.g., an input control device) is the leader, and a portion of the manipulating assembly 210 (e.g., a manipulator arm or other repositionable structure) is the follower.

In some examples, the repositionable structure includes a base manipulator and multiple instrument manipulators coupled to the base manipulator. In some examples, the repositionable structure includes a single instrument manipulator and no serial coupling of manipulators. In some examples, the repositionable structure includes a single instrument manipulator coupled to a single base manipulator. In some examples, the computer-assisted system can include a moveable-base that is cart-mounted or mounted to an operating table, and one or multiple manipulators mounted to the moveable base.

The manipulating assembly 210 can be used to introduce a set of instruments to a work site through a single port 230 (e.g., using a cannula is shown) inserted in an aperture. In a medical scenario, the work site can be on or within a body of a patient, and the aperture can be a minimally invasive incision or a natural body orifice. The port 230 can be free-floating, held in place by a fixture, or held by a linkage 222. The linkage 222 can be coupled to additional joints and links 214, 220 of the manipulating assembly 210, and these additional joints and links 214, 220 can be mounted on a base 212. The linkage 222 can further include a manipulator-supporting link 224. A set of manipulators 226 can couple to the manipulator-supporting link 224. The repositionable structure that can be moved to follow commands from the user input system 250 can include one or more of any of the following: the linkage 222, additional joints and links 214, 220, base 212, manipulator-supporting link 224, and/or any additional links or joints coupled to the foregoing joints or links. Each of the manipulators 226 can include a carriage (or other instrument-coupling link) configured to couple to an instrument, and each of the manipulators 226 can include one or more joint(s) and/or link(s) that can be driven to move the carriage. For example, a manipulator 226 can include a prismatic joint that, when driven, linearly moves the carriage and any instrument(s) coupled to the carriage. This linear motion can be along (parallel to) an insertion axis that extends through port 230.

The additional joints and additional links 214, 220 can be used to position the port 230 at the aperture or another position. FIG. 2 shows a prismatic joint for vertical adjustment (as indicated by arrow "A") and a set of rotary joints for horizontal adjustment (as indicated by arrows "B" and "C") that can be used to translate a position of a hardware RCM. The linkage 222 is used to pivot the port 230 (and the instruments disposed within the port at the time) in yaw, pitch, and roll angular rotations about the hardware RCM located in proximity to port 230 as indicated by arrows D, E, and F, respectively, without translating the hardware RCM.

Actuation of the degrees of freedom provided by joint(s) of the instrument(s) can be provided by actuators disposed in, or whose motive force (e.g., linear force or rotary torque) is transmitted to, the instrument(s). Examples of actuators include rotary motors, linear motors, solenoids, and/or the like. The actuators can drive transmission elements in the manipulating assembly 210 and/or in the instruments to control the degrees of freedom of the instrument(s). For example, the actuators can drive rotary discs of the manipulator that couple with drive elements (e.g., rotary discs, linear slides) of the instrument(s), where driving the driving elements of the instruments drives transmission elements in the instrument that couple to move the joint(s) of the instrument, or to actuate some other function of the instrument, such as a degree of freedom of an end effector. Accordingly, the degrees of freedom of the instrument(s) can be controlled by actuators that drive the instrument(s) in accordance with control signals. The control signals can be determined to cause instrument motion or other actuation as determined automatically by the system, as indicated to be commanded by movement or other manipulation of the input control devices, or any other control signal. Furthermore, appropriately positioned sensors, e.g., encoders, potentiometers, and/or the like, can be provided to enable measurement of indications of the joint positions, or other data that can be used to derive joint position, such as joint velocity. The actuators and sensors can be disposed in, or transmit to or receive signals from, the manipulator(s) 226. Techniques for manipulating multiple instruments in a computer-assisted system are described more fully in International Patent Application No. PCT/US2021/047374, filed Aug. 24, 2021, and entitled "METHOD AND SYSTEM FOR COORDINATED MULTIPLE-TOOL MOVEMENT USING A DRIVABLE ASSEMBLY," which is incorporated herein by reference.

While a particular configuration of the manipulating assembly 210 is shown in FIG. 2, those skilled in the art will appreciate that embodiments of this disclosure can be used with any design of manipulating assembly or other repositionable structure. For example, a manipulating assembly can have any number and any types of degrees of freedom, can be configured to couple or not couple to an entry port, can optionally use a port other than a cannula, such as a guide tube, and/or the like.

In the example shown in FIG. 2, the user input system 250 includes one or more input devices 252 configured to be operated by the operator 298. In the example shown in FIG. 2, the one or more input devices 252 are contacted and manipulated by the hands of the operator 298, with one input device for each hand. Examples of such hand-input-devices include any type of device manually operable by human user, e.g., joysticks, trackballs, button clusters, and/or other types of haptic devices typically equipped with multiple degrees of freedom. Position, force, and/or tactile feedback devices (not shown) can be employed to transmit position, force, and/or tactile sensations from the instruments back to the hands of the operator 298 through the input devices 252.

The input devices 252 are supported by the user input system 250 and are shown as mechanically grounded, and in other implementations can be mechanically ungrounded. An ergonomic support 256 can be provided in some implementations; for example, FIG. 2 shows an ergonomic support 256 including forearm rests on which the operator 298 can rest his or her forearms while manipulating the input devices 252. In some examples, the operator 298 can perform tasks at a work site near the manipulating assembly 210 during a procedure by controlling the manipulating assembly 210 using the input devices 252.

A display unit 254 is included in the user input system 250. The display unit 254 can display images for viewing by the operator 298. The display unit 254 can provide the operator 298 with a view of the worksite with which the manipulating assembly 210 interacts. The view can include stereoscopic images or three-dimensional images to provide a depth perception of the worksite and the instrument(s) of the manipulating assembly 210 in the worksite. The display unit 254 can be moved in various degrees of freedom to accommodate the viewing position of the operator 298 and/or to provide control functions. Where a display unit (such as the display unit 254 is also used to provide control functions, such as to command the manipulating assembly 210, the display unit also includes an input device (e.g., another input device 252).

When using the user input system 250, the operator 298 can sit in a chair or other support, position his or her eyes to see images displayed by the display unit 254, grasp and manipulate the input devices 252, and rest his or her forearms on the ergonomic support 256 as desired. In some implementations, the operator 298 can stand at the station or assume other poses, and the display unit 254 and input devices 252 can differ in construction, be adjusted in position (height, depth, etc.), and/or the like.

As described herein, the manipulating assembly 210 includes a first joint set of drivable joints that are by mechanical configuration constrained to produce motion that does not translate the hardware RCM, such that the first joint set of drivable joints are not designed to move the hardware RCM. The manipulating assembly 210 further includes a second joint set of drivable joints that are by mechanical configuration capable of moving the hardware RCM. In some examples, the operator 298 may want to move the RCM relative to, such as a position located proximal to 262 or distal to 264, the hardware RCM. In order to reduce motion of the portion of the repositionable structure (or instrument supported by the repositionable structure) at the entry and/or to address the need to move the RCM for other reasons, the disclosed embodiments allow for setting a virtual (or software) RCM at or near the entry where the software RCM is different from the hardware RCM. The disclosed embodiments utilize, as appropriate, motion in the second joint set in combination with motion in the first joint set to keep the software RCM at the selected position for the RCM. In some instances, a graphical user interface assists the operator 298 of the computer-assisted system in setting (registering for the system) the position of the software RCM. The graphical user interface further assists the operator 298 in determining the status of the software RCM, in terms of whether the software RCM has been set, whether a condition is inhibiting the ability of the repositionable structure to maintain the software RCM, and/or whether a condition affecting the software RCM has changed.

Figure 3A:
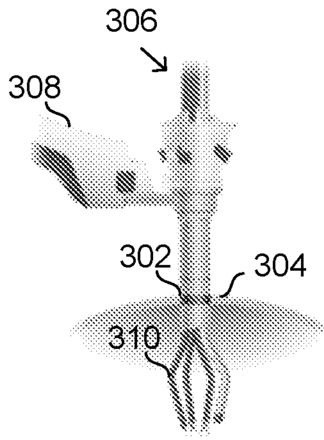
FIGS. 3A-3C illustrate various configurations of portions of a computer-assisted system (and/or instrument(s) supported by the computer-assisted system) in accordance with one or more embodiments.
Figure 3B:
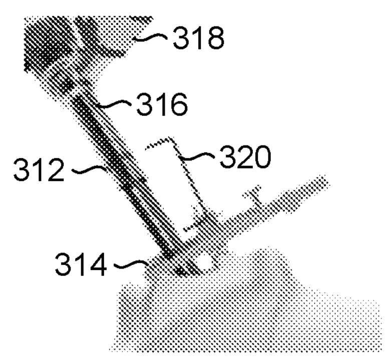
Figure 3C:
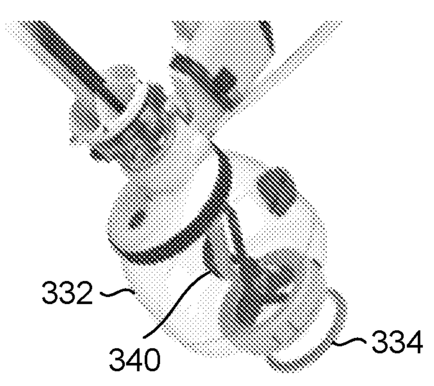

FIGS. 3A-3C illustrate various configurations of portions of a computer-assisted system (and/or instrument(s) supported by the computer-assisted system) in accordance with one or more embodiments. As shown in FIG. 3A, a first configuration includes a cannula 306 and a hardware RCM 302 that is placed at the entry 304 into a workspace. The repositionable structure of FIG. 3A includes a cannula mount 308 that helps support and move the cannula 306. One or more instruments 310 are supported by the repositionable structure, and extended through the cannula 306 and into the workspace through the entry 304. During operation without a software RCM offset from the hardware RCM, movement of the cannula 306 is typically constrained so that the cannula 306 is restricted to pivoting about the hardware RCM 302, and the effective RCM coincides with the hardware RCM 302, and remains in a fixed position relative to space (and if the entry 304 does not move relative to space, in a fixed position relative to the entry 304). In some embodiments, the instruments are not able to easily reach a "dead zone" extending some distance from the hardware RCM, such as due to physical obstacles or mechanical design. As a result, the repositionable structure in such configurations may be unable to easily perform operations in this dead zone. In addition, in some embodiments, the fixed location of the RCM also increases the difficulty of the instruments in reaching or performing procedures in other areas, such as in spaces farther away from the fixed RCM.

As shown in FIG. 3B, a second configuration includes a cannula 316 that includes a hardware RCM 312 that is placed proximal to the entry 314 into the workspace. The hardware RCM 312 and the entry 314 into the workspace are separated by a distance 320. The repositionable structure includes a cannula mount 318 that that helps support and move the cannula 316. One or more instruments (not shown in FIG. 3B) are extended through the cannula 316 and into the workspace through the entry 314. The configuration of FIG. 3B can be employed for procedures that involve operating instruments closer to the entry 314 than is possible with the configuration of FIG. 3A. In a medical example, such a configuration may be useful for certain procedures involving transoral robotic surgery (TORS), urosurgery (URO), colorectal surgery (CR), thoracic surgery (THOR), nipple-sparing mastectomy (NSM), and/or the like. In the configuration shown in FIG. 3B, if the cannula mount 318 moves the cannula 316 such that the cannula 316 pivots about the hardware RCM 312, then the cannula 316 can move relative to the entry 314. This large offset between the hardware RCM 312 and the entry 314 can result in various undesirable repositionable structure or instrument behaviors. Examples of less desirable behaviors include collision of the instruments with the material surrounding the entry 314, less intuitive instrument motion, more limited instrument motion, haptic and/or other feedback transmitted to the operator 298 that the operator 298 may find to be confusing and/or disorienting, difficulty when exchanging one instrument with another instrument, and/or the like.

As shown in FIG. 3C, a third configuration includes an access port 332 that does not include a cannula. Techniques for manipulating multiple instruments in a system fitted with an access port are described more fully in International Patent Application Publication No. WO 2021/067461 entitled "SINGLE PORT INSTRUMENT ACCESS DEVICE," which is incorporated herein by reference. The access port 332 allows one or more instruments 340 to be placed and manipulated very close to, or outside of the entry 334 into the workspace. The access port 332 is configured to maintain pressure within the access port 332, which can be useful for insufflating the workspace. Like the configuration of FIG. 3D, the access port 332 of FIG. 3C can be employed for procedures that involve operating instruments closer to the entry 334 than is possible with the configuration of FIG. 3A. The access port 332 allows the one or more instruments 340 to pivot about a hardware RCM. However, in the case of a configuration with an access port 332, the position of the hardware RCM can be difficult to determine for a human observer. Further, where the hardware RCM is offset from the entry 334, undesirable repositionable structure or instrument behaviors, as described in conjunction with FIG. 3B.

The disclosed embodiments provide an apparatus and method for setting a software RCM that is offset from the hardware RCM. With a software RCM offset from the hardware RCM, the computer-assisted system causes motions that hold the software RCM (and not the hardware RCM) fixed in space.

Figure 4:
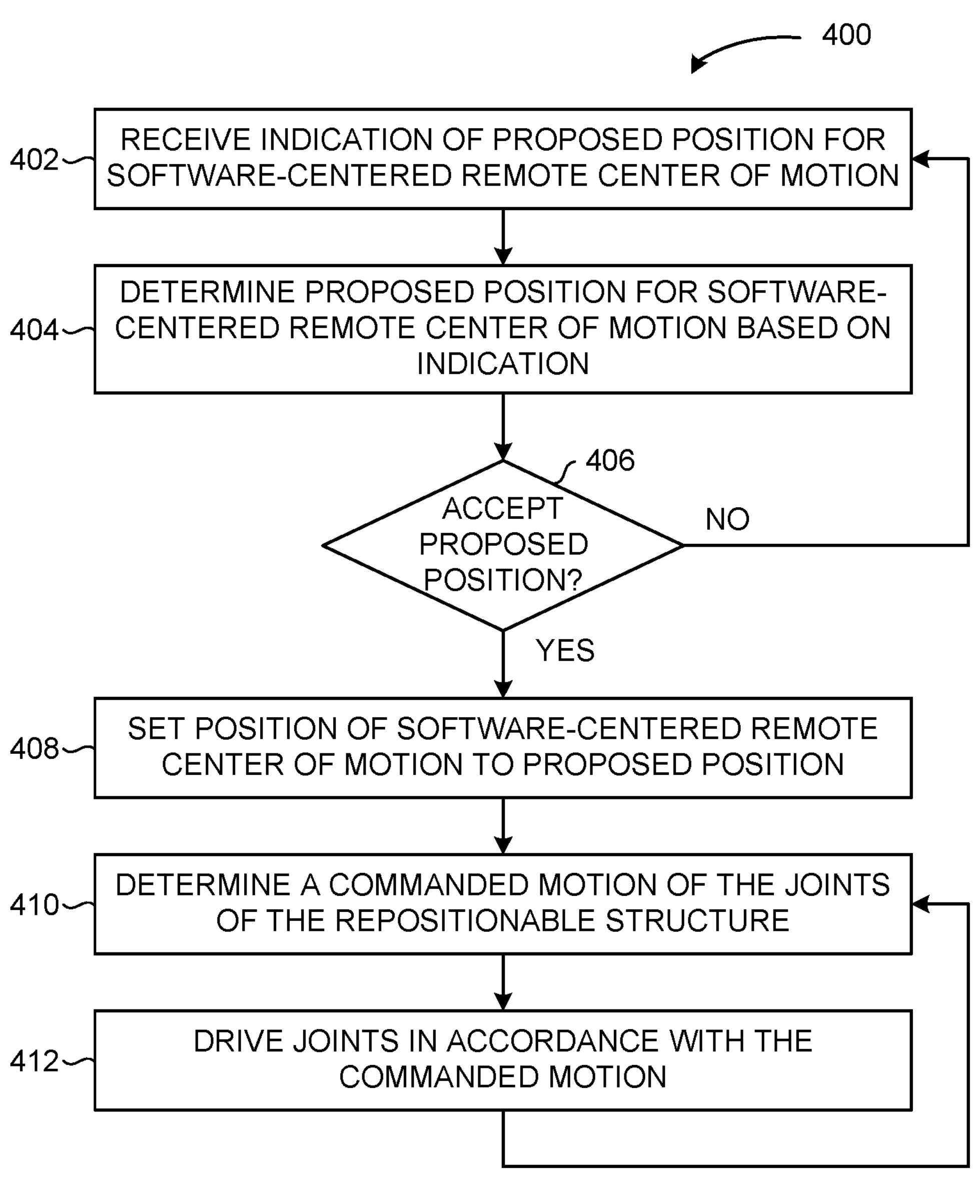
FIG. 4 is a flow diagram of method steps for controlling a repositionable structure relative to a software RCM in accordance with one or more embodiments.

FIG. 4 is a flow diagram of method steps for controlling a repositionable structure relative to a software RCM in accordance with one or more embodiments. Although the method steps are described in conjunction with the systems of FIGS. 1-3C and 7A-7C, persons of ordinary skill in the art will understand that any system configured to perform the method steps, in any order, is within the scope of the present disclosure. One or more of the processes 402-412 of method 400 can be implemented, at least in part, in the form of executable code stored on non-transient, tangible, machine-readable media. This executable code, when executed by one or more processors (e.g., the processor 150 in the control unit 140), can cause the one or more processors to perform one or more of the processes 402-412. In some embodiments, method 400 can be performed by a module, such as the control module 170. In some embodiments, method 400 can be used by a repositionable structure of a computer-assisted system to employ a software RCM that is different from a hardware RCM that is constrained based on the mechanical configuration of the repositionable structure. Prior to and/or during a procedure, the operator 298 is able to select a software RCM, where the software RCM is a position in the workspace about which one or more instruments are to be pivoted during teleoperation.

Figure 7A:
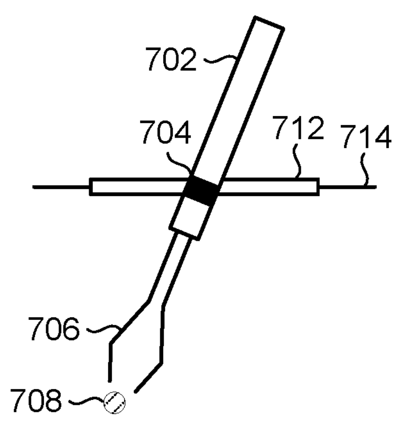
FIGS. 7A-7C illustrate various geometric relationships between a hardware RCM and a software RCM of a repositionable structure in accordance with one or more embodiments.
Figure 7B:
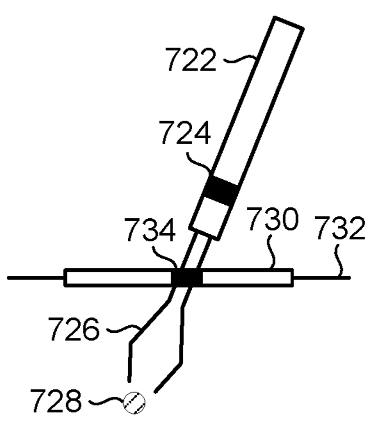
Figure 7C:
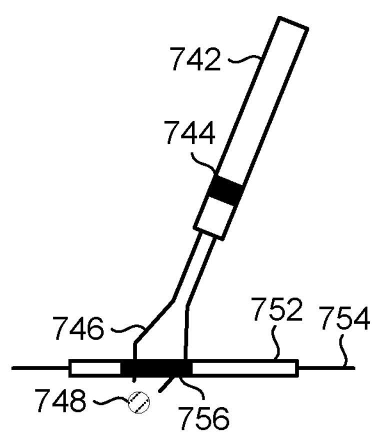

Aspects of method 400 are described via reference to FIGS. 7A-7C, which illustrate various geometric relationships between a hardware RCM and a software RCM of a repositionable structure in accordance with one or more embodiments. As will be understood, the geometric relationship between RCM positions (e.g. hardware RCM positions, default RCM positions where such are not hardware RCM positions, proposed software RCM positions, etc.) can comprise any appropriate geometric relationship. For example, a geometric relationship between a hardware RCM and a proposed software RCM position can comprise any one or more of the following: a minimum distances separating the positions, separation distances along one or more axes (e.g., X, Y, Z axes if a Cartesian coordinate system is used) between the positions, a direction pointing from the hardware RCM and the proposed software RCM, a direction pointing from the proposed software RCM to the hardware RCM, an area of a circle or volume of a sphere defined by rotating the proposed software RCM about the hardware RCM, etc.

As a specific example, in some instances, the geometric relationship comprises a proposed distance between the hardware RCM and the proposed position. The proposed distance may be measured in any appropriate manner, such as measured along a direction parallel to an alignment axis associated with the repositionable structure, and/or along an offset axis perpendicular to the alignment axis. In some instances, the proposed position for the software RCM is acceptable when such proposed distance is less than a threshold distance. Such threshold distance can be set at design, at manufacture, at initialization, during a procedure, etc. Such threshold distance can be static, or vary with parameters such as the type of procedure to be performed by the repositionable structure, type of instrument installed on (or to be installed on) the repositionable structure, stage of procedure, positions of joints or links of the repositionable structure, etc.

Further, it is understood that the examples of FIGS. 7A-7C and that other values, shapes, behaviors, and/or the like depicted in FIGS. 7A-7C may be different for different input devices, different repositionable structures, different follower instruments, different DOFs, different procedures, and/or the like.

In some examples, a control module, such as control module 170, can default to requesting or requiring that the operator 298 set a software RCM. The control module 170 can default to requesting or requiring the operator 298 to set a software RCM when certain particular accessories are employed or otherwise deployed for use with the computer-assisted system. As a specific example, the control module 170 can request the operator 298 to set a software RCM in response to one or more accessory ports being coupled to the computer-assisted system, as shown in FIG. 3C. Additionally or alternatively, the control module 170 can default to requesting or requiring the operator 298 to set a software RCM prior to or when performing particular procedures. Example procedures include those that access a target within the workspace that is more proximal and/or distal from the area accessible when the hardware RCM is employed. Such procedures include TORS, URO, CR, THOR, NSM, and/or the like. As a specific example, the control module 170 can request the operator 298 to set a software RCM in response to an indication such procedure is to be performed by the computer-assisted system (e.g. the procedure is beginning or underway, a particular stage of such procedure is commencing or underway, etc.)

In some examples, the control module 170 generates a request to the operator 298 to select or reselect the software RCM under certain conditions, such as when multiple instruments have been installed on the repositionable structure, when multiple instruments are installed in the cannula, when multiple instruments are inserted into the workspace, when a duration of time has passed since the current position of the software RCM was last set, and/or the like. Additionally or alternatively, the control module 170 generates a request to the operator 298 to select or reselect the software RCM when the repositionable structure and/or one or more instruments collide with material surrounding or near the entry into the workspace of the repositionable structure. The control module 170 can detect such collisions in any appropriate way, such as by ascertaining forces on the repositionable structure and/or one or more instruments, determining that a force received by the instrument or by a cannula used with the instrument satisfies an RCM reset condition, detecting position errors of the repositionable structure and/or one or more instruments near the entry into the workspace, and/or the like. Additionally or alternatively, the control module 170 generates a request to the operator 298 to select or reselect the software RCM when a range of motion limit in one or more of the joints in the second joint set is reached or approached. Additionally or alternatively, the control module 170 generates a request to the operator 298 to select or reselect the software RCM after the operator 298 has performed port clutching that moves the hardware RCM more than a nominal or threshold amount. Additionally or alternatively, the control module 170 generates a request to the operator 298 to select or reselect the software RCM at the command of the operator 298.

In some examples, the control module 170 determines that a software RCM setting is optional. In such examples, if the operator 298 does not set a software RCM, then the control module 170 defaults to using the hardware RCM (the hardware RCM in this case providing a "default position" or "default setting" for the RCM). In some examples, the control module 170 determines that the software RCM is not to be moved during the procedure. In such examples, the control module 170 can remove the option to set the software RCM after the operator 298 initially sets the software RCM.

At a process 402, control module 170, receives an indication of a proposed position for a software RCM such as by detecting an input from one or more input devices, in response to being manipulated by the operator 298. For example, the input devices can be contacted and manipulated by the hands of the operator 298, such as with one input device for each hand. Examples of such hand-input-devices include any type of device manually operable by human user, e.g., joysticks, trackballs, button clusters, and/or other types of haptic devices typically equipped with multiple degrees of freedom. The input devices are supported by a user input system and can be mechanically grounded or mechanically ungrounded. The changes in position and/or orientation (e.g., pose) of one or more input devices in the reference frame of the input devices are detected and translated into one or more motion commands. Depending upon the implementation, the pose of the input device and the current velocity of the input device can include one or more pose variables corresponding to the positional and/or orientational DOFs of the input device.

In some examples, the control module 170 can receive the indication of the proposed position prior to the beginning of a procedure, such as during installation of one or more instruments into a cannula, access port, and/or the like. Additionally or alternatively, the control module 170 can receive the indication of the proposed position at any point during a procedure. The control module 170 can receive the indication of the proposed position via any one or more of a variety of technically feasible modalities. In some examples, the operator 298 provides the indication of the proposed position by using a portion of the instrument to indicate the desired position of the software RCM. In so doing, the operator 298 can physically move the instrument by directly manipulating one or more joints of the manipulating assembly 210. Additionally or alternatively, the operator can move the instrument by remotely manipulating one or more joints of the manipulating assembly 210 via input controls located on the user input system 250. In some examples, the operator 298 places a portion of the instrument at a static position about which one or more instruments are to be pivoted during teleoperation. When the instrument is at the desired position, the operator 298 generates a selection input associated with the instrument, such as by pressing a button, speaking an audio command, selecting a graphical control element on a graphical user interface (GUI) screen, and/or the like. The position of the portion of the instrument at the time of the selection input is the position about which one or more instruments are to be pivoted during teleoperation. In some examples, the operator 298 can select a position at the entry into the workspace. In a medical example, the position can be at an incision in the body wall, at a natural orifice such as the mouth, and/or the like. Additionally or alternatively, the operator 298 can select another position, located proximal or distal from the entry into the workspace.

In some examples, the operator 298 dynamically traces a portion of the instrument around an area where the software RCM is desired. In this approach, the operator 298 traces the distal portion, such as a distal tip and/or any other relevant portion of the selected instrument, around the perimeter of an area of interest, such as the perimeter of the entry into the workspace. As used herein, references to the distal portion of an instrument refers to any relevant portion of the selected instrument, whether or not the relevant portion comprises the distal tip of the instrument. In some examples, the operator 298 can more accurately indicate the proposed position and/or more accurately trace around the perimeter of an area of interest when the instrument used to determine the indication of the proposed position of the software RCM is straight or nearly straight. Accordingly, the control module 170 can determine whether the instrument is straight or nearly straight. If the instrument is not sufficiently straight, then the control module 170 optionally generates a prompt to the operator 298 to manually straighten the instrument being employed to provide the indication of the proposed position of the software RCM. Additionally or alternatively, the control module 170 generates commands to articulate the instrument until the instrument is straight or nearly straight. This additional step of straightening the instrument being employed to determine the software RCM can be performed in the context of the methods described in conjunction with FIG. 5 and/or FIG. 6.

In some examples, the control module 170 determines the indication of the proposed position of the software RCM based on a position of a distal portion of the instrument installed in a cannula, an entry guide, an accessory port, and/or the like, as described herein. If the cannula, entry guide, accessory port, and/or the like supports multiple instruments, then the control module 170 can select the distal portion of any installed instrument that is supported by the repositionable structure of the computer-assisted system. More specifically, the control module 170 can select the distal portion of the first installed instrument and/or can select the distal portion of any subsequently installed instrument based on any criteria. In so doing, the control module 170 can select the distal portion of a particular instrument based on the type of the instrument and/or the geometry of the instrument. In some examples, the control module 170 can restrict the selection to a distal portion of an instrument that is not an imaging device. By imposing this restriction, the control module 170 allows the imaging device to be available for the operator 298 to view the workspace as the operator 298 is determining the indication of the proposed position of the software RCM.

In some examples, the control module 170 selects an instrument for indicating the proposed position of the software RCM from a set of instruments supported by the repositionable structure. The control module 170 selects an instrument based on an order of installation such as selecting a first-installed instrument of the set of instruments, a selection of a first-installed non-imaging instrument of the set of instruments, selection of an instrument of the set of instruments installed immediately after an imaging instrument of the set of instruments, and/or the like.

In some examples, the operator 298 can indicate the proposed position of the software RCM based on various criteria other than the distal portion of an instrument. In some examples, the operator 298 indicate the proposed position of the software RCM based on positions of various indicia associated with the workspace, such as a natural fiducial present in the workspace or a fiducial marker that has been applied and/or added to the workspace. The fiducial marker can be a radio frequency identifier (RFID), a two-dimensional (2D) or three-dimensional (3D) barcode, a special instrument that expands at the distal end of the instrument to the size and shape of the entry into the workspace, and/or the like.

In some examples, the operator 298 can indicate the proposed position of the software RCM by extending a probe from the repositionable structure, or an accessory coupled to the repositionable structure. The control module 170 commands an actuator system to extend a probe supported by the repositionable structure until the probe stops in response to reaching an extension limit, receiving an operator command, contacting a portion of the probe with an object in a workspace accessible to an instrument supported by the repositionable structure, and/or the like. The position of the probe and/or accessory provides the indication of the proposed position of the software RCM. The accessory coupled to the repositionable structure can include a cannula, an entry guide, an accessory port, and/or the like.

In some examples, the operator 298 manually enters the indication of the proposed position of the software RCM into an interface associated with the computer-assisted system.

At a process 404, the processor, determines the indication of the proposed position for the software RCM based on the indication received at process 402. The control module 170 can determine the indication of the proposed position of the software RCM based on a position of any technically feasible device, or portion thereof, associated with the computer-assisted system.

In some examples, when the indication of the proposed position is associated with a static position of distal portion of the selected instrument during process 402, the control module 170 determines the indication of the proposed position of the software RCM based on the static position of the distal portion of the selected instrument. Additionally or alternatively, in some examples, the control module 170 can determine whether the operator 298 is tracing the distal portion of the selected instrument around the perimeter of an area of interest. The set of positions can define a two-dimensional shape (2D), a two-dimensional shape with depth information (2D+), a three-dimensional shape (3D), and/or the like. The control module 170 makes this determination based on data received from various sensors, such as by analyzing images received from cameras aimed towards the operator 298 in order to analyze the motions of the operator 298. When the indication of the proposed position is associated with a set of positions generated as the distal portion of the selected instrument is traced around the perimeter of an area of interest during process 402, the control module 170 determines the indication of the proposed position of the software RCM based on the dynamic position of the distal portion of the selected instrument. The control module 170 detects data associated with the positions of the distal portion of the selected instrument as the operator 298 traces the distal portion of the selected instrument around the perimeter of the area of interest.

In some examples, the control module 170 analyzes the set of positions for consistency with an expected motion path, an expected shape, an expected region of interest, and/or the like. In this regard, the set of positions can be consistent with the distal portion tracing a perimeter of an area, tracing a surface of a volume, and/or the like. In some examples, the control module 170 does not analyze the set of positions for consistency with an expected motion path, an expected shape, an expected region of interest, and/or the like. In this regard, the set of positions can be based on detecting the start of a motion by the operator 298 and then detecting that the motion of the operator 298 has stopped. Additionally or alternatively, the set of positions can be based on detecting positions during a particular time period after receiving a corresponding instruction from the operator, and/or the like.

Based on this data, the control module 170 determines an indication of a proposed position for the software RCM. In some examples, the control module 170 determines the indication of the proposed position based on an aggregation of positions of the distal portion of the selected instrument during the tracing, such as by averaging the positions, determining a centroid of the traced positions, and/or the like.

In some examples, when the indication of the proposed position is associated with one or more natural or applied fiducials during process 402, the control module 170 determines the indication of the proposed position of the software RCM based on the position of the one or more natural or applied fiducials. In that regard, the workspace can include multiple natural or applied fiducials, where one fiducial applies to set the software RCM during initial setup of the procedure and one or more additional fiducials are employed to change the software RCM at certain points during the procedure.

In some examples, when the indication of the proposed position is associated with an object of a characteristic object, tissue, and/or other material during process 402, the control module 170 determines the distance to, or the position of, the characteristic object, tissue, and/or other material by employing triangulation techniques. Such triangulation techniques can employ various sensors and devices, including an endoscope and/or other imaging device with stereo vision, depth cameras, shape sensors, and/or other depth and/or position sensors. Via the triangulation techniques, the control module 170 receives images of an object present in the workspace accessible to an instrument supported by the repositionable structure. The control module 170 receives the images from multiple sensors and determines a triangulated position of the object based on the images. The control module 170 determines the indication of the proposed position of the software RCM based on the triangulated position.

In some examples, when the indication of the proposed position is associated with a probe extended into the workspace during process 402, the control module 170 determines the indication of the proposed position of the software RCM based on position data associated with the probe.

In some examples, the control module 170 determines the indication of the proposed position of the software RCM by additionally projecting the indication from process 402 (or a derivation of the indication, such as a time-based derivative) onto an alignment axis. The alignment axis can be collinear with an aggregation of axes of a set of instruments supported by a set of instrument manipulators. Additionally or alternatively, the alignment axis can be collinear with an aggregation of translational axes of the set of instrument manipulators, each translational axis being associated with an instrument insertion motion of a prismatic joint of an instrument manipulator of the set of instrument manipulators. Additionally or alternatively, the alignment axis can be collinear with a central axis for a cannula mounted to the repositionable structure.

More specifically, in some examples, the alignment axis is an axis associated with the cannula, entry guide, accessory port, and/or the like. The control module 170 determines the alignment axis via various techniques. In some examples, the control module 170 determines the alignment axis based on a translational axis of a prismatic joint of the manipulating assembly 210 used to insert the instrument, cannula, and/or the like through the hardware RCM. Additionally or alternatively, the control module 170 determines the alignment axis based on a position of a center line and/or a roll axis of a shaft of the instrument supported by the manipulating assembly 210 and employed to select the position used to determine the software RCM. Additionally or alternatively, the control module 170 determines the alignment axis based on an aggregate of the center lines and/or roll axes of multiple instruments and/or translational axes of multiple prismatic joints of the manipulating assembly 210. Additionally or alternatively, the control module 170 determines the alignment axis based on a position of a center line and/or a roll axis of a cannula, guide tube, entry guide, and/or the like supported by the manipulating assembly 210, such as when multiple instruments are passed through the cannula, guide tube, entry guide, and/or the like.

At a process 406, the control module 170 determines whether to accept the indication of the proposed position from processes 402 and 404. In some examples, the control module 170 determines whether to accept the indication of the proposed position for the software RCM based on a geometric relationship between the hardware RCM and the indication of the proposed position for the software RCM.

In some examples, the control module 170 determines certain conditions for allowing the operator 298 to set an initial software RCM and/or for allowing the operator 298 to move the software RCM based on an operator selected position. The control module 170 can allow the operator 298 to set the software RCM within an allowed setting range by limiting the distance between the software RCM and the hardware RCM along an alignment axis associated with the cannula, entry guide, accessory port, and/or the like. Additionally or alternatively, the control module 170 can allow the operator 298 to set the software RCM within an allowed setting range by defining the software RCM within some safe range of the hardware RCM, such as when a lateral offset of the software RCM from the alignment axis is permitted. Additionally or alternatively, the control module 170 can allow the operator 298 to set the software RCM (or the control module 170 accepts the proposed software RCM position) when the control module 170 determines that the joints of the repositionable structure have sufficient range of motion with the software RCM set to the proposed position, to maintain the software RCM when an instrument supported by the repositionable structure is moved in a manner typical of a procedure to be performed by the instrument.

If the operator 298 attempts to set the software RCM outside the allowed setting range, then the control module 170 can perform various remedial actions. The control module 170 can determine that one or more sets of joints limits the acceptable range of motion needed to support the software RCM requested by the operator 298. If the control module 170 determines that the selected software RCM is not acceptable, then the control module 170 can revert to the position of the hardware RCM, to a default position (also referred to as a "default setting"), to an undefined position, and/or the like. Additionally or alternatively, the processor can maintain the software RCM at the previously selected software RCM. In addition, the control module 170 can generate a notice to the operator 298, such as one or more visual, audio, and/or haptic alerts, that the control module 170 has performed one of these remedial actions. Additionally or alternatively, the control module 170 can prompt the operator 298 to override the current settings, thereby allowing the operator 298 to set the software RCM at a position that is outside the allowed setting range.

If, at process 406, the control module 170 determines to not accept the indication of the proposed position, then the method returns to process 402. If, however, the control module 170 determines to accept the indication of the proposed position, then the method proceeds to process 408, where the control module 170 sets the software RCM to the indication of the proposed position.

At a process 410, the control module 170 determines a commanded motion of the joints of the repositionable structure. The commanded motion can affect movement so as to pivot the cannula and/or one or more instruments about the hardware RCM or the software RCM. In that regard, FIGS. 7A-7C, illustrate various geometric relationships between a hardware RCM and a software RCM of a repositionable structure in accordance with one or more embodiments. In the example shown in FIG. 7A, a portion of a repositionable structure 702 is positioned such that the hardware RCM 704 is located near the entry 712 to the workspace 714. In this example, the software RCM has not been set, or has not been set to differ from the hardware RCM. Thus, the control module 170 determines a commanded motion that pivots the cannula and/or one or more instruments about the hardware RCM 704. The commanded motions provide access to a target 708 that is located at a distance from the entry 712 that is accessible by one or more instruments 706.

In the example shown in FIG. 7B, a target 728 is located closer to the entry 730 of the workspace 732 than can be easily accessed by the one or more instruments 726 in the configuration shown in FIG. 7A. In order to perform a procedure involving such a target 728, the portion of a repositionable structure 722 is positioned such that the hardware RCM 724 is located proximal to the entry 730 to the workspace 732. In this example, the operator 298 has set a software RCM 734 that is different from the hardware RCM 724 to a position near the entry 730 to the workspace 732. A first portion of the one or more instruments 726 is located proximal to the entry 730 to the workspace 732, and a second portion of the one or more instruments 726 is located distal to the entry 730 to the workspace 732. The control module 170 determines a commanded motion of the first and second joint sets of the repositionable structure that pivots the portion of a repositionable structure 722 and/or one or more instruments about the software RCM 734, while moving when needed the hardware RCM 724. The commanded motions provide easier access to a target 728 that is located closer to the entry 730 relative to the target 708 of FIG. 7A.

In the example shown in FIG. 7C, a target 748 is located even closer to the entry 752 of the workspace 754 than can be easily accessed by the one or more instruments 746 in the configuration shown in FIG. 7A or FIG. 7B. In some examples, the target 748 is located in a region that is inaccessible when the one or more instruments 726 are inserted into the workspace 732, as shown in the configuration of FIG. 7B. In order to perform a procedure involving such a target 748, the portion of a repositionable structure 742 is positioned such that the hardware RCM 744 is located proximal to the entry 752 to the workspace 754. In the example of FIG. 7C, the one or more instruments 746 are retracted further from the entry 752 so that distal portions of the one or more instruments 746 are inserted into the workspace 754. In this example, the operator has set a software RCM 756 that is different from the hardware RCM 744 and different from the software RCM 734 described in conjunction with FIG. 7B. Specifically, in the example of FIG. 7C, the software RCM 756 has been set to be near the entry 752 to the workspace 754. A first portion of the one or more instruments 746 is located proximal to the entry 752 to the workspace 754, and a second portion of the one or more instruments 746 is located distal to the entry 752 to the workspace 754. The control module 170 determines a commanded motion of the first and second joint sets of the repositionable structure that pivots the one or more instruments about the software RCM 756, while moving when needed the hardware RCM 744. The commanded motions provide easier access to a target 748 that is located closer to the entry 752 relative to the target 708 of FIG. 7A or the target 728 of FIG. 7B.

In general, the joints of the repositionable structure include a first joint set, where each joint of a first joint set is physically restricted to joint motions that maintain a position of the hardware RCM. The joints of the repositionable structure further include a second joint set, where each joint of a second joint set of the plurality of joints is physically configured to perform joint motions capable of translating the position of the hardware RCM. When the control module 170 is determining a commanded motion of the joints with respect to a software RCM, the commanded motion can include motions of any one or more joints of the first joint set and/or any one or more joints of the second joint set, in any combination. The commanded motion can move the hardware RCM but maintain the position of the software RCM. In that regard, maintaining the position of the software RCM incudes generating little or no motion of the repositionable structure and/or the instruments at the software RCM. In some examples, the commanded motion can generate some movement of the software RCM within a relatively small tolerance due to manufacturing tolerances, rounding errors in calculations, motor timing, and/or the like. The commanded motion can include moving one or more instruments and/or moving a portion of the repositionable structure. Such a commanded motion can move the one or more instruments and/or the repositionable structure along an alignment axis going through the software RCM. Additionally or alternatively, the commanded motion can pivot the one or more instruments and/or the repositionable structure about the software RCM.

In some examples, the joints of the repositionable structure can include additional joints that are not specifically included in either the first joint set or the second joint set, such as one or more joints for causing some other motion of the repositionable structure or any instruments supported by the repositionable structure (e.g., opening and closing jaws of an instrument). Stated another way, the first joint set and/or the second joint set can be interspersed with intervening joints, where the intervening joints have attributes that are different from the attributes of the first joint set and/or the second joint set. In that regard, the first joint set are by mechanical configuration constrained to produce motion that does not translate the hardware RCM. However, in some examples, some configurations can include a drivable joint that can translate the hardware RCM, where the drivable joint can be located between two of the joints in the first joint set. Additionally or alternatively, the second joint set of drivable joints are by mechanical configuration capable of translating the hardware RCM. However, in some examples, some configurations can include a drivable joint that is constrained to produce motion that does not translate the hardware RCM, where the drivable joint can be located between two of the joints in the second joint set.

At a process 412, and upon determining the commanded motion, the control module 170 drives the joints of the repositionable structure in accordance with the commanded motion. The method 400 then proceeds to process 410 to determine additional commanded motions. Under various conditions, the method 400 can alternatively return to process 402 to receive an indication of a proposed new position for the software remote center. In some examples, the control module 170 can request or require the operator 298 to indicate a new proposed location for the software RCM when certain specific accessories are employed during a procedure, such as accessory port, as shown in FIG. 3C. Additionally or alternatively, the control module 170 can request or require the operator 298 to indicate a new proposed location for the software RCM when the operator performs certain procedures that access a target within the workspace that is more proximal and/or distal from the area accessible when the current software RCM is employed. In some examples, the control module 170 can request or require the operator 298 to indicate a new proposed location for the software RCM when all instruments are installed in the cannula, when all instruments are inserted into the workspace, when a defined time period has elapsed, and/or the like. In some examples, the control module 170 can request or require the operator 298 to indicate a new proposed location for the software RCM when the repositionable structure and/or one or more instruments collide with material surrounding or near the entry into the workspace. In some examples, the control module 170 can request or require the operator 298 to indicate a new proposed location for the software RCM when a range of motion limit in one or more of the joints in the second joint set is reached or approached. In some examples, the control module 170 can request or require the operator 298 to indicate a new proposed location for the software RCM after the operator 298 has performed port clutching, which moves the hardware RCM more than a nominal or threshold amount. In some examples, the control module 170 can request or require the operator 298 to indicate a new proposed location for the software RCM at the command of the operator 298.

In some examples, the control module 170 is configured to request or require the operator 298 to indicate a new proposed location for the software RCM in response to an occurrence of one or more of the following events: an instrument used to provide the indication of the proposed position for the RCM has been uninstalled from the repositionable structure, all instruments have been uninstalled from the repositionable structure, a portion of the repositionable structure has reached or nearing a range of motion limit of the repositionable structure, or the computer-assisted system has undergone a mid-procedure restart. Alternatively, in some examples, the control module 170 can be configured to maintain the current position of the software RCM despite an occurrence of one or more of the following events: an instrument used to provide the indication of the proposed position for the RCM has been uninstalled from the repositionable structure, all instruments have been uninstalled from the repositionable structure, a portion of the repositionable structure has reached or nearing a range of motion limit of the repositionable structure, or the computer-assisted system has undergone a mid-procedure restart.

As discussed above and further emphasized here, FIG. 4 is merely an example which should not unduly limit the scope of the claims. One of ordinary skill in the art would recognize many variations, alternatives, and modifications. In some embodiments, various conditions can result in a selected software RCM being disabled. In some examples, the control module 170 disables setting of the current position of the software RCM when the operator 298 is externally manipulating the repositionable structure. For example, when a first operator is externally manipulating the repositionable structure (or the control module 170 is in a mode that facilitates external manipulation of the repositionable structure), the control module 170 can allow the setting of the current position of the software RCM based on input by the first operator, while disabling the setting of the current position of the software RCM based on input by a second operator. The input provided by the second operator may be through external manipulation of the repositionable structure, through input to a user input system, etc. As another example, when a first operator is commanding movement of the repositionable structure using a user input system separate from the repositionable structure (or the control module 170 is in a mode that facilitates external manipulation of the repositionable structure), the control module 170 can allow the setting of the current position of the software RCM based on input by the first operator, while disabling the setting of the current position of the software RCM based on input by a second operator. The input provided by such second operator can be through external manipulation of the repositionable structure, through input to another part of the user input system or another user input system, etc.

The following paragraphs describe examples in which a hardware RCM provides a default position (also called "default setting") for the RCM. Similar techniques can also be used where the default position for the RCM is other than the hardware RCM. Such default positions that are not hardware RCMs may be previously defined software RCM settings, such as an initial position of the RCM set at a beginning of a procedure, during a procedure, etc.

In some examples, when a software RCM is set and active, the control module 170 can revert to using the position of the hardware RCM. In such examples, the control module 170 can revert to using the position of the hardware RCM at the end of a procedure (e.g. in response to the completion of a procedure that was previously being performed by the repositionable structure), when the cannula removed from the computer-assisted system (e.g. in response to a removal of a cannula from use with the repositionable structure), when the accessory port removed from the computer-assisted system (e.g. in response to a removal of an accessory port previously mounted to the repositionable structure), when remote center management setting is disabled or becomes disables, if the operator 298 attempts to move the software RCM remote center beyond safety range, and/or the like. In such examples, the control module 170 can generate a prompt to the operator 298 to set the software RCM before proceeding.

In some examples, the control module 170 can refrain from reverting to the hardware RCM under certain conditions, including when the operator 298 removes the instrument used to set the software RCM, when the operator 298 removes some, but not all, of the installed instruments, when the repositionable structure is not at a range of motion limit, when the operator 298 restarts a procedure during the performance of the procedure, and/or the like.

In some examples, two or more operators 298 perform and/or assist in the performance of a procedure using the computer-assisted system. In such examples, a first operator 298 can be located at the user input system 250, while a second operator 298 can be located at the manipulating assembly 210. In order to reduce confusion among the multiple operators, the control module 170 can disable the first operator 298 from setting the software RCM when the second operator 298 is performing a port clutching procedure.

In some examples, the control module 170 determines a manual range of motion and/or clearance of the repositionable structure after the software RCM is set. In such examples, the control module 170 can direct the operator 298 to perform the additional process of clutching and manually rotating the repositionable structure and/or one or more instruments around the software RCM in order to establish the range of motion expected during the procedure.

In some examples, the repositionable structure does not have a hardware RCM. In such examples, the processor can set a default software RCM (also referred to as a "default position" or "default setting" for the RCM) that is dependent on the type of computer-assisted system, the type of one or more installed instrument, the type of procedure, the preference of the operator 298, and/or the like.

Figure 5:
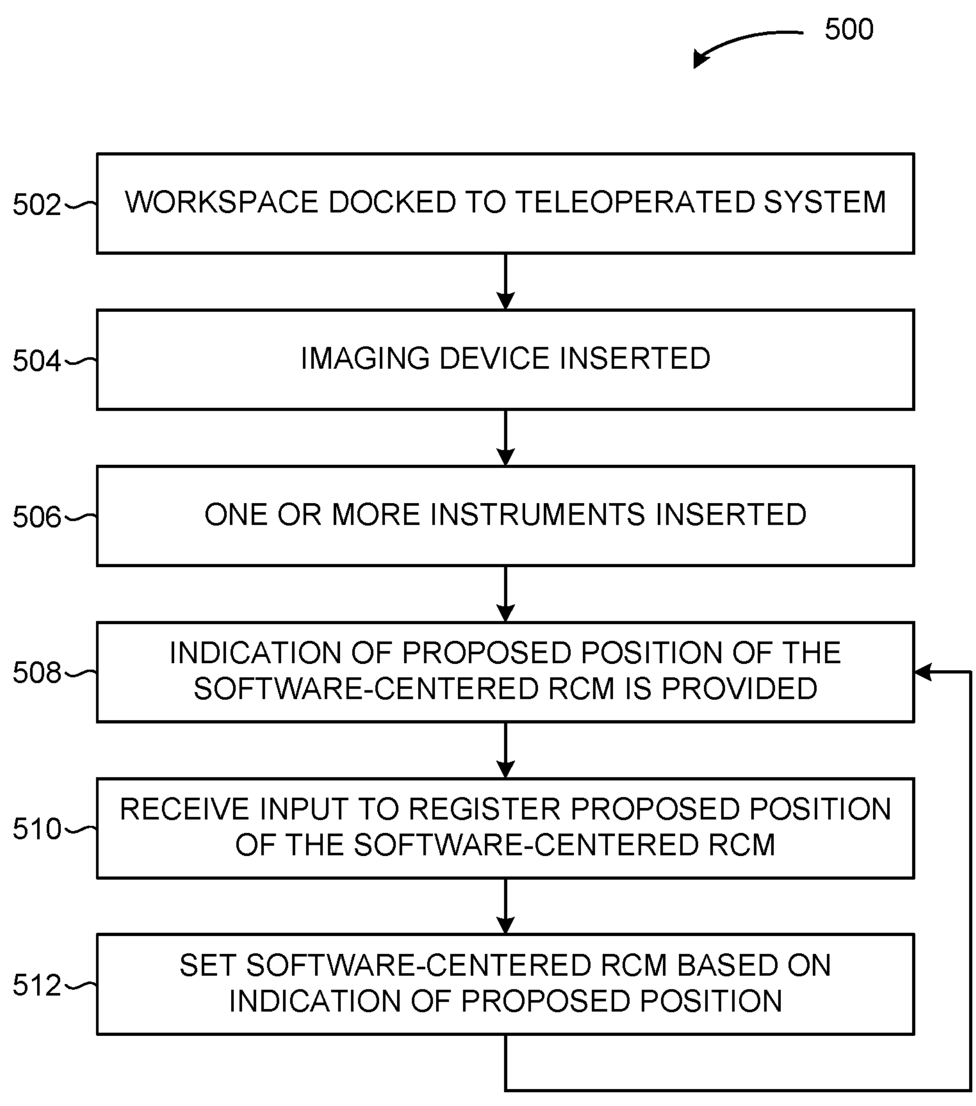
FIG. 5 is a flow diagram of method steps for setting a software RCM in accordance with one or more embodiments.

FIG. 5 is a flow diagram of method steps for setting a software RCM in accordance with one or more embodiments. Although the method steps are described in conjunction with the systems of FIGS. 1-3C and 7A-7C, persons of ordinary skill in the art will understand that any system configured to perform the method steps, in any order, is within the scope of the present disclosure. In particular, processes 502-506 are optional, and any one or more of processes 502-506 can be omitted within the scope of the present disclosure. One or more of the processes 502-512 of method 500 can be implemented, at least in part, in the form of executable code stored on non-transient, tangible, machine-readable media. This executable code, when executed by one or more processors (e.g., the processor 150 in the control unit 140), can cause the one or more processors to perform one or more of the processes 502-512. In some embodiments, method 500 can be performed by a module, such as the control module 170. In some embodiments, method 500 can be used by a repositionable structure of a computer-assisted system to establish a software RCM that is different from, and has a geometric relationship to, a hardware RCM that is constrained based on the mechanical configuration of the repositionable structure.

At a process 502, an operator 298 locates a workspace relative to a computer-assisted system, such as the computer-assisted system 100 of FIG. 1 or the computer-assisted system 200 of FIG. 2. The operator 298 locates the workspace by moving cannula, guide tube, or entry guide supported by a repositionable structure of the computer-assisted system to be accessible to the entry into the workspace. In a medical example, the workspace is the body of a patient and the entry is an incision, natural orifice such as the mouth of the patient, and/or the like.

At an optional process 504, the operator 298 inserts an imaging device into the cannula, guide tube, entry guide, access location, etc. The imaging device can be a camera, an endoscope, and/or the like. In some examples, the imaging device enables the operator 298 to view the workspace and the entry into the workspace while selecting the software RCM. In some examples, the operator 298 selects the software RCM without the aid of an imaging device. For example, if the computer-assisted system is fitted with an access port, an operator 298 standing near the repositionable structure can visualize the entry into the workspace and the instruments directly. The operator 298 can position an instrument to identify the proposed position of the software RCM without using the imaging device.

At a process 506, the operator 298 inserts one or more instruments into a cannula, guide tube, or entry guide supported by a repositionable structure of the computer-assisted system. In some examples, the cannula, guide tube, or entry guide supports a single instrument. In such examples, the operator 298 inserts the single instrument into the cannula, guide tube, or entry guide. Alternatively, the cannula, guide tube, or entry guide supports multiple instruments. In such examples, the operator 298 inserts any one or more instruments into the cannula, guide tube, or entry guide, up to and including the number of instruments supported by the cannula, guide tube, or entry guide.

At a process 508, the operator 298 provides an indication of the proposed position of the software RCM. In some examples, the operator 298 places a portion of one of the installed instruments, such as the distal portion of the instrument, at the entry into the workspace. Alternatively, the operator 298 places a portion of one of the installed instruments at a different position that is relevant to the procedure being performed. Alternatively, the operator 298 can employ any of the techniques described with respect to process 402 for indicating the proposed position of the software RCM. When indicating the proposed position, the operator can employ a port clutching mode, where a joint set is allowed to move so that the operator can manually change the hardware RCM.

At a process 510, a control module, such as control module 170, receives an input from the operator 298 to register the proposed position for the software RCM. In some examples, the operator 298 generates the indication via a selection input associated with the instrument, such as by pressing a button, speaking an audio command, selecting a graphical control element on a GUI screen, and/or the like.

At a process 512, the control module 170 sets the software RCM to the indication of the proposed position, as described in conjunction with processes 404-408 of FIG. 4. The control module 170 optionally generates one or more visual, audio, and/or haptic prompts to the operator 298 to indicate that the software RCM has been set. In some examples, to set the software RCM, the control module 170 projects the position (or a derivation of the position, such as a velocity or acceleration) of the distal portion of the instrument onto an alignment axis associated with an instrument, cannula, guide tube, or entry guide supported by the repositionable structure in order to determine the position of the software RCM. This process limits the software RCM to vary in only a single degree of freedom (DOF) from the hardware RCM.

In some examples, the control module 170 does not constrain the software RCM to be offset from the hardware RCM along only one axis, that is, along only a single degree of freedom. Instead, the software RCM can be offset from the hardware RCM along multiple degrees of freedom, such as a translation along the alignment axis and a translation along an offset axis perpendicular to the alignment axis. In such examples, the control module 170 sets the software RCM to the proposed position determined from the indication received during process 508. As a result, the control module 170 allows the software RCM to be offset laterally from the alignment axis. In these examples, the control module 170 does not project the proposed position to be located on the alignment axis.

The method 500 then proceeds to process 508, where the operator 298 optionally provides a new indication for the proposed position of the software RCM. In this manner, the operator 298 can select different software remote centers of motion as needed during different steps of the procedure.

Figure 6:
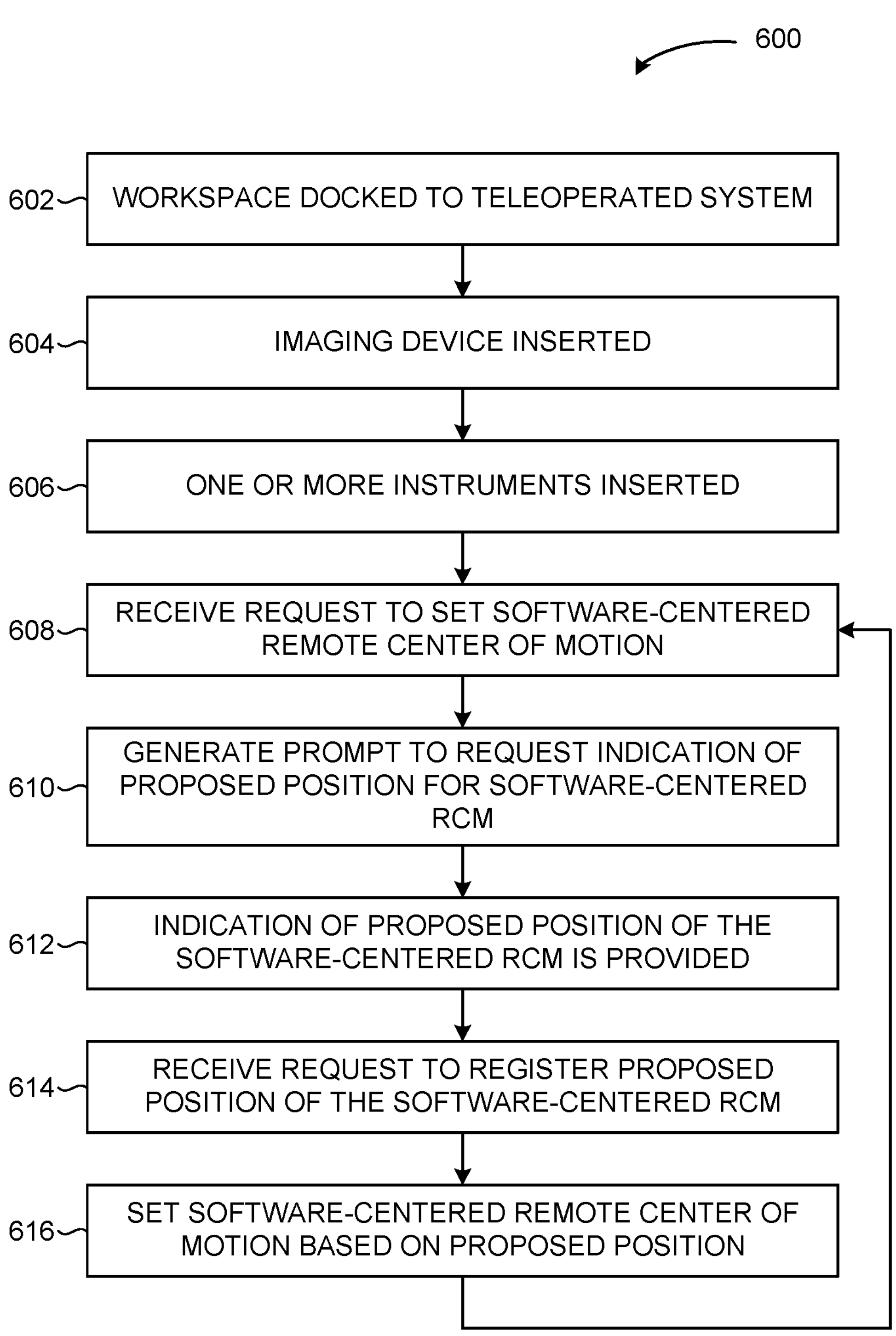
FIG. 6 is a flow diagram of method steps for setting a software RCM in accordance with one or more embodiments.

FIG. 6 is a flow diagram of method steps for setting a software RCM in accordance with one or more embodiments. Although the method steps are described in conjunction with the systems of FIGS. 1-3C and 7A-7C, persons of ordinary skill in the art will understand that any system configured to perform the method steps, in any order, is within the scope of the present disclosure. In particular, processes 602-606 are optional, and any one or more of processes 602-606 can be omitted within the scope of the present disclosure. One or more of the processes 602-616 of method 600 can be implemented, at least in part, in the form of executable code stored on non-transient, tangible, machine-readable media. This executable code, when executed by one or more processors (e.g., the processor 150 in the control unit 140), can cause the one or more processors to perform one or more of the processes 602-616. In some embodiments, method 600 can be performed by a module, such as the control module 170. In some embodiments, method 600 can be used by a repositionable structure to establish a software RCM that is different from, and has a geometric relationship to, a hardware RCM that is constrained based on the mechanical configuration of the repositionable structure. Further, method 600 can be used in applications where additional confirmation is desirable before setting the software RCM. Such applications include surgical applications where incorrectly setting the software RCM increases the risk of damage or injury to the patient or other applications where damage to the workspace can be significant, costly, and/or the like.

At a process 602, an operator 298 locates a workspace relative to a computer-assisted system, such as the computer-assisted system 100 of FIG. 1 or the computer-assisted system 200 of FIG. 2. The operator 298 locates the workspace by moving cannula, guide tube, or entry guide supported by a repositionable structure of the computer-assisted system to be accessible to the entry into the workspace. In a medical example, the workspace is the body of a patient and the entry is an incision, natural orifice such as the mouth of the patient, and/or the like.

At an optional process 604, the operator 298 inserts an imaging device into the cannula, guide tube, or entry guide. The imaging device can be a camera, an endoscope, and/or the like. In some examples, the imaging device enables the operator 298 to view the workspace and the entry into the workspace while selecting the software RCM. In some examples, the operator 298 selects the software RCM without the aid of an imaging device. For example, if the computer-assisted system is fitted with an access port, an operator 298 standing near the repositionable structure can visualize the entry into the workspace and the instruments directly. The operator 298 can position an instrument to identify the proposed position of the software RCM without using the imaging device.

At a process 606, the operator 298 inserts one or more instruments into a cannula, guide tube, or entry guide supported by a repositionable structure of the computer-assisted system. In some examples, the cannula, guide tube, or entry guide supports a single instrument. In such examples, the operator 298 inserts the single instrument into the cannula, guide tube, or entry guide. Alternatively, the cannula, guide tube, or entry guide supports multiple instruments. In such examples, the operator 298 inserts any one or more instruments into the cannula, guide tube, or entry guide, up to and including the number of instruments supported by the cannula, guide tube, or entry guide.

At a process 608, the operator 298 generates a request to set the position for a software RCM. In some examples, the operator 298 generates the request by activating a first input to enter a setting mode. The operator 298 generates the request via a selection input associated with the instrument, such as by pressing a button, speaking an audio command, selecting a graphical control element on a GUI screen, and/or the like. A control module, such as control module 170, receives the request from the operator 298.

At a process 610, the control module 170, generates a prompt to the operator 298. The prompt to the operator 298 requests the operator 298 to provide the indication of the proposed position of the software RCM. In some examples, the prompt requests the operator 298 to place a portion of one of the installed instruments, such as the distal portion of the instrument, at the entry into the workspace. Alternatively, the prompt to the operator 298 requests the operator 298 to place a portion of one of the installed instruments at a different position that is relevant to the procedure being performed. Alternatively, the prompt to the operator 298 requests the operator 298 to indicate the proposed position via any of the techniques described with respect to process 402 for indicating the proposed position of the software RCM.

At a process 612, the operator 298 provides an indication of the proposed position of the software RCM. In some examples, the operator 298 places the portion of one of the installed instruments at the entry into the workspace. Alternatively, the operator 298 places a portion of one of the installed instruments at a different position that is relevant to the procedure being performed. Alternatively, the operator 298 can employ any of the techniques described with respect to process 402 for indicating the proposed position of the software RCM. When indicating the proposed position, the operator can employ a port clutching mode, where a joint set are allowed to move so that the operator can manually change the hardware RCM.

At a process 614, the control module 170 receives a request from the operator 298 to register the proposed position of the software RCM. In some examples, the operator 298 generates the request by activating a second input and/or by activating the first input for a second time. The operator 298 generates the indication via a selection input associated with the instrument, such as by pressing a button, speaking an audio command, selecting a graphical control element on a GUI screen, and/or the like.

At a process 616, the control module 170 sets the software RCM to the indication of the proposed position, as described in conjunction with processes 404-408 of FIG. 4. If the operator 298 is remotely located from the manipulating assembly 210, then the control module 170 optionally requests confirmation input from the operator 298 located at the user input system 250 (also referred to as an "operator confirmation") before setting the register the position of the portion of one of the installed instruments. The control module 170 optionally generates one or more visual, audio, and/or haptic prompts to the operator 298 to indicate that the software RCM has been set. In some examples, to set the software RCM, the control module 170 projects the position of the distal portion of the instrument onto an alignment axis associated with an instrument, cannula, guide tube, or entry guide supported by the repositionable structure in order to determine the position of the software RCM. This process limits the software RCM to vary in only one degree of freedom (DOF) from the hardware RCM.

In some examples, the control module 170 does not constrain the software RCM to be offset from the hardware RCM along only one axis, that is, along only one degree of freedom. In such examples, the control module 170 sets the software RCM to the proposed position determined from the indication received during process 612. As a result, the control module 170 allows the software RCM to be offset laterally from the alignment axis. In these examples, the control module 170 does not project the proposed position to be located on the alignment axis.

The method 600 then proceeds to process 608 where the operator 298 optionally provides a new indication for the proposed position of the software RCM. In this manner, the operator 298 can select different software remote centers of motion as needed during different steps of the procedure.

Some examples of control units, such as the control unit 140 of FIG. 1 can include non-transient, tangible, machine-readable media that include executable code that when executed by one or more processors (e.g., the processor 150 of FIG. 1) can cause the one or more processors to perform the processes of method 400. Some common forms of machine-readable media that can include the processes of method 400 are, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the invention should be limited only by the following claims, and it is appropriate that the claims be construed broadly and in a manner consistent with the scope of the embodiments disclosed herein.

What is claimed is:

1. A computer-assisted system comprising:

an input control;

a repositionable structure comprising a plurality of joints, wherein each joint of a first joint set of the plurality of joints is physically restricted to joint motions that maintain a position of a hardware remote center of motion (RCM) of the repositionable structure, and wherein each joint of a second joint set of the plurality of joints is physically configured to perform joint motions capable of translating the position of the hardware RCM; and a processing system communicatively coupled to the input control and the repositionable structure, the processing system configured to:

receive an indication of a proposed position for a software RCM of the repositionable structure, determine whether to accept the proposed position based on a geometric relationship between the position of the hardware RCM and the proposed position, in response to a determination to accept the proposed position, set a current position of the software RCM based on the proposed position, after setting the current position of the software RCM based on the proposed position and in response to an indication to move the repositionable structure with a desired motion, determine a commanded motion of the plurality of joints to move the repositionable structure in accordance with the desired motion while maintaining the current position of the software RCM, and drive the plurality of joints in accordance with the commanded motion.

2. The computer-assisted system of claim 1, wherein the processing system is further configured to:

determine the proposed position based on a detected position of a distal portion of an instrument; or determine the proposed position based on a selected instrument of a plurality of instruments supported by the repositionable structure, the selected instrument selected based on an order of installation of the plurality of instruments.

3. The computer-assisted system of claim 1, wherein:

the indication of the proposed position comprises a plurality of positions of a distal portion of an instrument supported by the repositionable structure as the distal portion is moved; or the indication of the proposed position comprises a fiducial present in a workspace, the workspace being accessible to the instrument supported by the repositionable structure, and the processing system is further configured to: determine the proposed position based on a position of the fiducial; or the indication of the proposed position comprises one or more images of an object present in the workspace, and the processing system is further configured to: determine the proposed position based on a position of the object determined using the one or more images.

4. The computer-assisted system of claim 1, wherein to receive the indication of the proposed position, the processing system is configured to:

command an actuator system to extend a probe supported by the repositionable structure until the probe stops in response to reaching an extension limit, receiving an operator command, or contacting an object in a workspace, the workspace being accessible to an instrument supported by the repositionable structure; and determine the proposed position based on a position of a portion of the probe when the probe is stopped.

5. The computer-assisted system of claim 1, wherein the processing system is further configured to:

determine the proposed position by projecting the indication or a derivation of the indication onto an alignment axis associated with the repositionable structure.

6. The computer-assisted system of claim 1, wherein to set the current position of the software RCM based on the proposed position, the processing system is configured to:

determine the software RCM to be offset from the hardware RCM along a single degree of freedom.

7. The computer-assisted system of claim 1, wherein to set the current position of the software RCM based on the proposed position, the processing system is configured to:

request operator confirmation to register the proposed position; and set the current position in response to receiving the operator confirmation to register the proposed position.

8. The computer-assisted system of claim 1, wherein:

the geometric relationship comprises a proposed distance between the hardware RCM and the proposed position; and to determine whether to accept the proposed position, the processing system is configured to: determine whether the proposed distance is less than a threshold distance.

9. The computer-assisted system of claim 1, wherein to determine whether to accept the proposed position, the processing system is configured to:

determine whether the second joint set has a sufficient range of motion to, if the software RCM is set to the proposed position, maintain the software RCM when an instrument supported by the repositionable structure is moved in a manner typical of a procedure to be performed by the instrument.

10. The computer-assisted system of claim 1, wherein the processing system is further configured to:

in response to a determination not to accept the proposed position, set the current position of the software RCM to the hardware RCM, to a default position, or to an undefined position.

11. The computer-assisted system of claim 1, wherein the processing system is further configured to: generate a request for the indication of the proposed position in response to:

determining that a particular accessory is deployed for use with the computer-assisted system; or determining that a particular procedure is to be performed by the computer-assisted system.

12. The computer-assisted system of claim 1, wherein the processing system is further configured to: generate a request for the indication of the proposed position in response to:

determining that a plurality of instruments has been installed on the repositionable structure; or determining that a duration of time has passed since the current position was last set; or determining that the hardware RCM has moved by more than a threshold amount; or determining that a collision has occurred between material near an entry into a workspace of the repositionable structure and the repositionable structure; or determining that a collision has occurred between the material near the entry and an instrument supported by the repositionable structure; or determining that a force received by the instrument or by a cannula used with the instrument satisfies an RCM reset condition; or determining that one or more joints included in the second joint set is at or near a range of motion limit.

13. The computer-assisted system of claim 1, wherein the processing system is further configured to: set the current position of the software RCM to a default position in response to determining an occurrence of at least one event selected from the group consisting of:

a completion of a procedure previously being performed by the repositionable structure;

a removal of a cannula from use with the repositionable structure; and a removal of an accessory port previously mounted to the repositionable structure.

14. The computer-assisted system of claim 1, wherein the processing system is further configured to:

when a first operator is externally manipulating the repositionable structure, disable setting of the current position of the software RCM based on input by a second operator but allow the setting of the current position of the software RCM based on input by the first operator; or disable setting of the current position of the software RCM when the repositionable structure is being externally manipulated.

15. A method comprising:

receiving, by a processing system, an indication of a proposed position for a software remote center of motion (RCM) for a repositionable structure;

determining, by the processing system, whether to accept the proposed position based on a geometric relationship between a position of a hardware RCM of the repositionable structure and the proposed position;

in response to a determination to accept the proposed position, setting, by the processing system, a current position of the software RCM based on the proposed position;

after setting the current position of the software RCM based on the proposed position and in response to an indication to move the repositionable structure with a desired motion, determining, by the processing system, a commanded motion of a plurality of joints to move the repositionable structure in accordance with the desired motion while maintaining the current position of the software RCM; and driving, by the processing system, the plurality of joints in accordance with the commanded motion, wherein each joint of a first joint set of the plurality of joints is physically restricted to joint motions that maintain the position of the hardware RCM of the repositionable structure, and wherein each joint of a second joint set of the plurality of joints is physically configured to perform joint motions capable of translating the position of the hardware RCM.

16. The method of claim 15, further comprising:

determining, by the processing system, the proposed position based on a position of a distal portion of an instrument supported by the repositionable structure; or determining, by the processing system, the proposed position based on a selected instrument of a plurality of instruments supported by the repositionable structure, the selected instrument selected based on an order of installation of the plurality of instruments.

17. The method of claim 15, further comprising:

determining, by the processing system, the proposed position based on a selected instrument of a plurality of instruments supported by the repositionable structure, the selected instrument selected based on an order of installation of the plurality of instruments;

wherein selecting the instrument based on the order of installation comprises:

selecting a first-installed instrument of the plurality of instruments; or selecting a first-installed non-imaging instrument of the plurality of instruments; or selecting an instrument of the plurality of instruments installed immediately after an imaging instrument of the plurality of instruments.

18. The method of claim 15, further comprising:

determining, by the processing system, the proposed position by projecting the indication or a derivation of the indication onto an alignment axis associated with the repositionable structure.

19. The method of claim 15, wherein setting the current position of the software RCM based on the proposed position comprises:

determining the software RCM to be offset from the hardware RCM along a single degree of freedom.

20. The method of claim 15, wherein:

the geometric relationship comprises a proposed distance between the hardware RCM and the proposed position; and determining whether to accept the proposed position comprises: determining whether the proposed distance is less than a threshold distance.

21. The method of claim 15, wherein determining whether to accept the proposed position comprises:

determining whether the second joint set has a sufficient range of motion to, if the software RCM is set to the proposed position, maintain the software RCM when an instrument supported by the repositionable structure is moved in a manner typical of a procedure to be performed by the instrument.

22. The method of claim 15, further comprising:

in response to a determination not to accept the proposed position, setting, by the processing system, the current position of the software RCM to the hardware RCM, to a default position, or to an undefined position.

23. The method of claim 15, further comprising: generating, by the processing system, a request for the indication of the proposed position in response to:

determining, by the processing system, that a particular accessory is deployed for use with a computer-assisted system; or determining, by the processing system, that a particular procedure is to be performed by the computer-assisted system.

24. The method of claim 15, further comprising: generating, by the processing system, a request for the indication of the proposed position in response to:

determining, by the processing system, that one or more joints included in the second joint set is at or near a range of motion limit.

25. The method of claim 15, further comprising: setting, by the processing system, the current position of the software RCM to a default position in response to determining an occurrence of at least one event selected from the group consisting of:

a completion of a procedure previously being performed by the repositionable structure;

a removal of a cannula from use with the repositionable structure; and a removal of an accessory port previously mounted to the repositionable structure.

26. The method of claim 15, further comprising:

when a first operator is externally manipulating the repositionable structure, disabling, by the processing system, setting of the current position of the software RCM based on input by a second operator but allowing the setting of the current position of the software RCM based on input by the first operator; or disabling, by the processing system, setting of the current position of the software RCM when the repositionable structure is being externally manipulated.

27. One or more non-transitory machine-readable media comprising a plurality of machine-readable instructions which, when executed by one or more processors associated with a computer-assisted system, are adapted to cause the one or more processors to perform a method comprising:

receiving an indication of a proposed position for a software remote center of motion (RCM) for a repositionable structure;

determining whether to accept the proposed position based on a geometric relationship between a position of a hardware RCM of the repositionable structure and the proposed position;

in response to a determination to accept the proposed position, setting a current position of the software RCM based on the proposed position;

after setting the current position of the software RCM based on the proposed position and in response to an indication to move the repositionable structure with a desired motion, determining a commanded motion of a plurality of joints to move the repositionable structure in accordance with the desired motion while maintaining the current position of the software RCM; and driving the plurality of joints in accordance with the commanded motion, wherein each joint of a first joint set of the plurality of joints is physically restricted to joint motions that maintain the position of the hardware RCM of the repositionable structure, and wherein each joint of a second joint set of the plurality of joints is physically configured to perform joint motions capable of translating the position of the hardware RCM.

28. The one or more non-transitory machine-readable media of claim 27, wherein setting the current position of the software RCM based on the proposed position comprises:

determining the software RCM to be offset from the hardware RCM along a single degree of freedom.

29. The one or more non-transitory machine-readable media of claim 27, wherein:

the geometric relationship comprises a proposed distance between the hardware RCM and the proposed position; and determining whether to accept the proposed position comprises: determining whether the proposed distance is less than a threshold distance.

* * * * *